United States Patent
Wahlgren et al.

(10) Patent No.: US 9,220,885 B2
(45) Date of Patent: Dec. 29, 2015

(54) PLACEMENT DEVICES THAT ENABLE PATIENTS TO ACCURATELY POSITION MEDICAL PATCHES AT TARGET LOCATIONS AND METHODS THEREFOR

(75) Inventors: Stephen B. Wahlgren, Easton, PA (US); Andrea Slater Tomko, Greentown, PA (US); Glenn H. Stahl, Collegeville, PA (US); Andrew Joseph March, Lake Forest, CA (US); Rochelle Kleinberg, New York, NY (US); Karin Elise Taylor, New York, NY (US); Martin J. Nohilly, Murray Hill, NJ (US); Michael William Ammerman, San Clemente, CA (US)

(73) Assignee: Ethicon, Inc., Somerville, NJ (US)

( * ) Notice: Subject to any disclaimer, the term of this patent is extended or adjusted under 35 U.S.C. 154(b) by 1586 days.

(21) Appl. No.: 12/642,176

(22) Filed: Dec. 18, 2009

(65) Prior Publication Data

US 2011/0152987 A1    Jun. 23, 2011

(51) Int. Cl.
*A61N 1/04*        (2006.01)
*A61N 1/05*        (2006.01)

(52) U.S. Cl.
CPC ........................................ *A61N 1/05* (2013.01)

(58) Field of Classification Search
USPC .................. 300/372, 382, 386, 393
See application file for complete search history.

(56) References Cited

U.S. PATENT DOCUMENTS

| | | | |
|---|---|---|---|
| 4,432,368 A | | 2/1984 | Russek |
| 5,042,481 A | * | 8/1991 | Suzuki et al. ................. 600/393 |
| 6,173,198 B1 | * | 1/2001 | Schulze et al. ................ 600/382 |
| 2005/0277998 A1 | | 12/2005 | Tracey et al. |
| 2006/0079792 A1 | * | 4/2006 | Finburgh et al. .............. 600/485 |
| 2006/0195153 A1 | | 8/2006 | DiUbaldi et al. |
| 2008/0097549 A1 | | 4/2008 | Colbaugh |

FOREIGN PATENT DOCUMENTS

| | | |
|---|---|---|
| EP | 2198915 | 6/2010 |
| GB | 2457025 | 8/2009 |
| WO | 2008062395 | 5/2008 |

OTHER PUBLICATIONS

Partial International Search Report for International Application No. PCT/US2010/059687, dated Mar. 4, 2011.
Copeding, co-owned U.S. Appl. No. 13/796,883, filed Mar. 12, 2013.

* cited by examiner

*Primary Examiner* — William Thomson
*Assistant Examiner* — Jeffrey Lipitz
(74) *Attorney, Agent, or Firm* — Cohen & Hildebrand, PLLC

(57) ABSTRACT

A placement device for a medical patch includes an alignment guide having a shaft with a first end having a first anatomical alignment marker and a second end having a second anatomical alignment marker, a swinging gate both pivotally and rotationally coupled with the first end of the shaft for selectively pivoting the gate toward and away from the shaft and rotating the gate between opposite sides of the shaft, whereby the gate has first and second major faces and a first opening extending through the gate between the first and second major faces. The placement device includes a spacer for selectively adjusting spacing between the gate and the first end of the shaft, and a flexible diaphragm having a flexible dome disposed within the first gate opening. At least one magnet is located in the center of the flexible dome for holding the medical patch within the flexible dome.

3 Claims, 29 Drawing Sheets

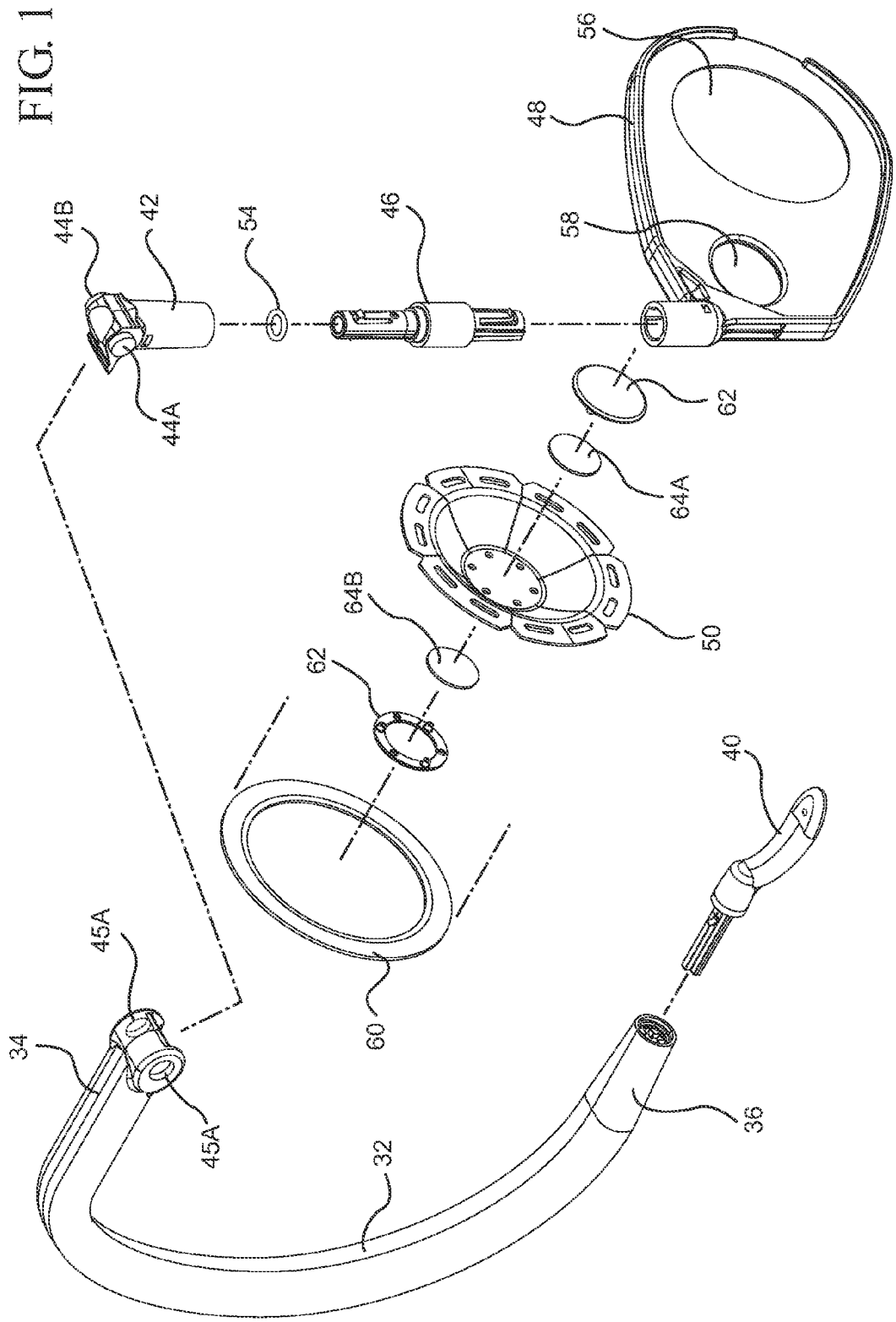

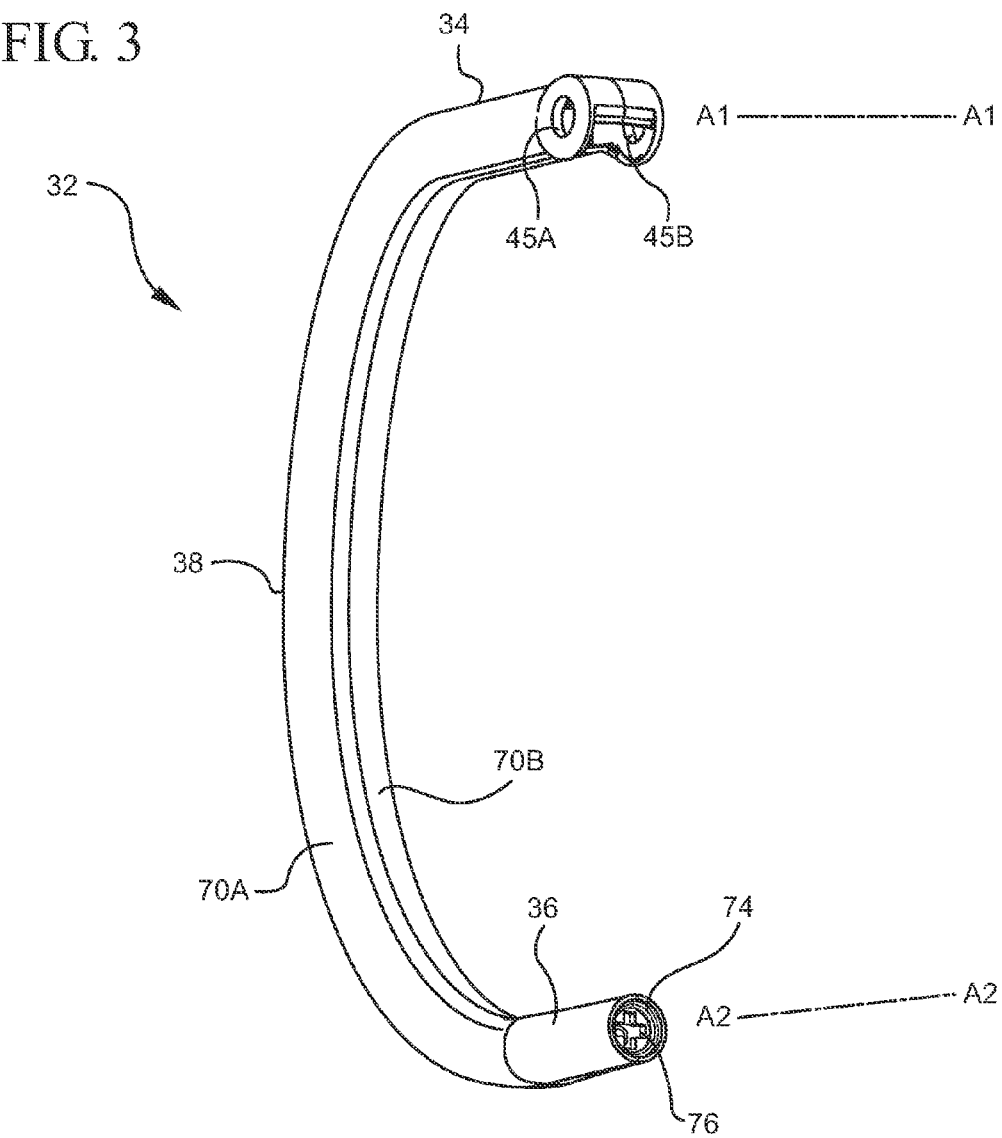
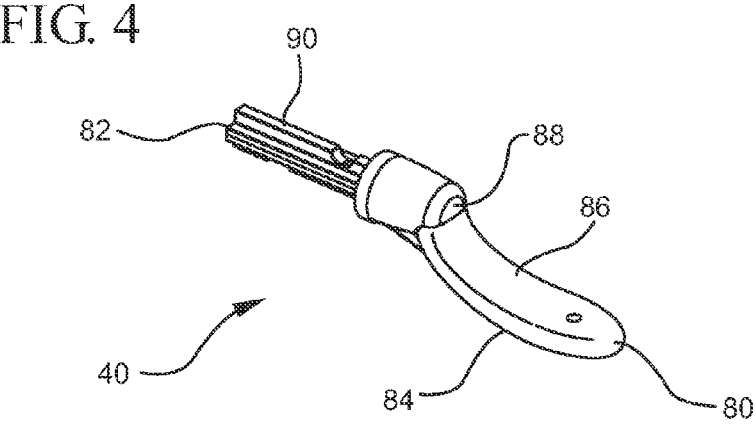

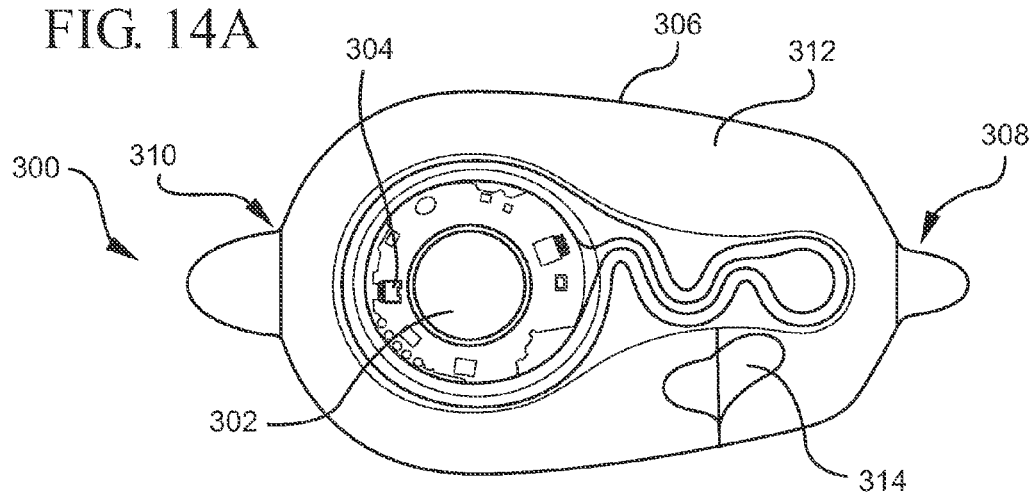
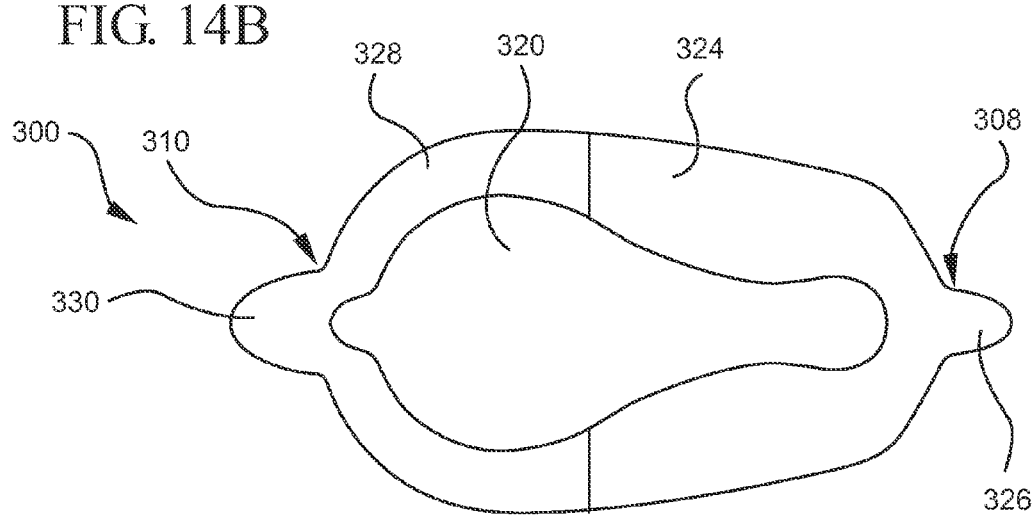
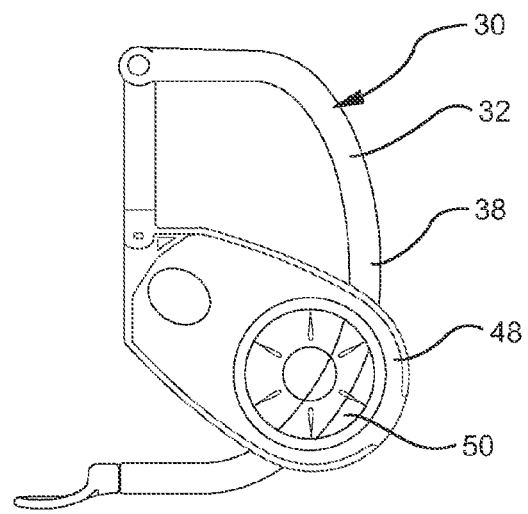

PLACEMENT DEVICES THAT ENABLE PATIENTS TO ACCURATELY POSITION MEDICAL PATCHES AT TARGET LOCATIONS AND METHODS THEREFOR

BACKGROUND OF THE INVENTION

1. Field of the Invention

The present invention generally relates to medical patches, and more specifically relates to placement devices and related methods that enable patients to align and apply a series of medical patches over target locations on a body without the assistance of a second person or medical personnel.

2. Description of the Related Art

Nerves are part of the peripheral nervous system of a human body. They convey sensory signals back and forth from the skin and body organs to the central nervous system. Nerves may become damaged due to wear and tear, physical injuries, infection, and/or the failure of the blood vessels surrounding the nerves. These functional defects may be accompanied by pain, numbness, weakness, and in some cases, paralysis. Other problems resulting from damaged nerves may include urinary and fecal incontinence.

Different tactics have been developed to treat the above-mentioned problems. For example, treating urinary incontinence may involve behavior modification such as urinating more frequently and wearing protective undergarments. In certain social situations, however, individuals may not be able to follow the practice of frequent urination or wearing protective undergarments. Another approach involves a medical therapy including taking prescribed drugs. This methodology may result in adverse side effects or drug interactions, however, that will ultimately require discontinuation.

Another technique for treating the above-noted conditions involves stimulating a nerve using an electro-medical device that is positioned near a target nerve. One such electro-medical device is commonly referred to as an Implantable Pulse Generator (IPG), which typically includes one or more electrodes, an electrical pulse generator, a battery, and a housing. The electrical pulse generator generates an electrical signal adapted to stimulate a target nerve. When the electrodes receive the signal from the generator, they draw energy from the battery and generate an electric field of suitable strength to stimulate the target nerve.

IPG's have proven to be somewhat effective for stimulating nerves, however, they are extremely invasive because they must be implanted inside a patient's body during a surgical procedure. IPG's also consume a significant amount of power, which may be due to an increase in electrical impedance between the electrodes, or an increase in electrical impedance between the electrodes and the IPG. Higher battery power consumption may also be caused by a phenomenon referred to as "desensitization of stimulus," whereby the human body responds to an applied external charge by offering a resistance to the applied external charge. The body resists the applied external charge by increasing the stimulation threshold for a target nerve, thereby rendering the earlier stimulus level ineffective. To overcome this problem, a more powerful charge must be generated, which consumes even more battery power, and which requires frequent replacement and/or recharging of the batteries.

In some nerve stimulation devices, it has been observed that the generated electric field spreads widely, affecting untargeted muscles and nerves along with the target nerve. The wide spreading of the electric field significantly reduces the strength of the electrical signal at the target nerve. In order to properly stimulate the target nerve, the strength of the electrical signal must be substantially increased, which requires the device to draw more power from the battery.

In view of the above drawbacks, there have been a number of efforts seeking to stimulate nerves in a more efficacious and non-invasive manner. For example, non-invasive selective nerve stimulation (SNS) medical patches are disclosed in commonly assigned U.S. Patent Publication Nos. 2005/0277998, filed Jun. 7, 2005, and 2006/0195153, filed Jan. 31, 2006, the disclosures of which are hereby incorporated by reference herein. Specifically, in one or more embodiments thereof, the '998 publication teaches a non-invasive, transcutaneous neurostimulation patch that generates and transmits a controlled, amplitude-modulated waveform comprising a carrier signal and a pulse envelope. The carrier waveform is designed to be of sufficient frequency to overcome attenuation due to tissue impedances. The pulse envelope contains specific pulse width, amplitude and shape information designed to stimulate specific nerves. In addition to nerve stimulation, medical patches may also be used for delivering pharmacological agents such as pain medication, drugs, and hormones.

Medical patches are often adhered to a patient's skin surface with an active or operating portion of the patch directed toward a target location on the patient. Over a period of time, the medical patches deliver the nerve stimulation or the pharmacological agents to the patient for achieving a therapeutic benefit. In some instances, a series of medical patches are applied to the patient, whereby a first medical patch applied by a medical professional is removed from a patient's skin and replaced with a second medical patch. Eventually, the second medical patch may be removed and replaced by a third medical patch and so on. The application of the second and subsequent medical patches is often done by the patient at home. Due to inexperience in properly placing replacement medical patches, the replacement medical patches may be improperly aligned over the target location on the patient, e.g. a particular nerve that is the target for nerve stimulation.

In view of the foregoing, there is a need for SNS medical patch placement devices and methods that provide for precise and repeatable placement of medical patches, whereby a series of medical patches are efficiently placed and precisely aligned over a target location on a patient's body. There also remains a need for improved medical patch systems that effectively stimulate target nerves and body parts, while not stimulating untargeted nerves and body parts. Furthermore, there remains a need for nerve stimulation devices that are less invasive, and that require less power to operate effectively, thereby minimizing the need to replace and/or recharge power sources.

There also remains a need for improved systems and methods for self-positioning and aligning medical patches that deliver pharmacological agents such as pain medication, drugs, and hormones. In addition, there is a need for placement devices that enables patients, while at home and unassisted, to self-locate and place medical patches over one or more target locations on the patient's body. In addition, there is a need for medical patch systems that enable patients to use their tactile senses to identify the various parts of the patch, especially in instances where the patches are not visible to the user.

SUMMARY OF THE INVENTION

In one embodiment, a medical patch placement device addresses the alignment and location issues faced by patients when attempting to apply medical patches at home with no assistance. In one embodiment, the placement device preferably provides a repeatable and accurate system for placing medical patches on a patient's body. In one embodiment, the placement device may be used for medical treatments other than nerve stimulation, such as drug delivery or pain management.

In one embodiment, the placement device for precisely placing medical patches includes a handle, an upper arm section, a lower curved section including a spoon-like cup, and a swinging patch holder or gate. In one embodiment, the spoon-like cup is designed to fit under the distal end of the sacrum at the point where the coccyx begins and curves inward (sacrococcygeal junction or tailbone). In one embodiment, the cup is preferably attached to the handle, and may be adjustable to accommodate patients having varying body types. The placement device includes at least one vertical adjustment mechanisms for making vertical adjustments to accommodate variations in anatomy (e.g. shorter or taller patients).

In one embodiment, the patient holds the placement device by the handle and uses it to manipulate the placement device to the correct position and to hold that position while the gate holding the medical patch is swung to the skin surface to attach the medical patch to the skin. In one embodiment, the top horizontal portion of the handle includes a hinge that enables a vertical element holding the gate to pivot away from the body as needed, which enables the placement device to accommodate patients having varying lower back/buttocks contours.

In one embodiment, the placement device includes a flexible diaphragm that is connected with the gate for holding a medical patch on the gate. The placement device preferably includes at least one magnet attached to the flexible diaphragm that is adapted to magnetically attract a portion of the medical patch that includes metal or that has magnetic properties. The gate also preferably includes at least one slot to hold the medical patch on the medial end thereof. The flexible diaphragm preferably includes a dome that may be flexed back and forth to either side of the gate to accommodate left or right side spinal patch placement. After the gate has been properly positioned on the back, the patch may be ejected from the gate by pushing the patch away from the dome and the magnet.

In one embodiment, a placement device for positioning a medical patch includes an alignment guide having a first anatomical alignment marker and a second anatomical alignment marker, and a gate adapted to hold a medical patch, the gate being coupled with the alignment guide for swinging between left and right sides of the alignment guide for positioning the patches on the left and right sides of a patient.

In one embodiment, the alignment guide preferably includes a handle having an upper end and a lower end, whereby the first anatomical alignment marker is located at the upper end of the handle and the second anatomical alignment marker is located at the lower end of the handle. In one embodiment, the handle has a C-shape configuration, and the first and second anatomical alignment markers are located at the free ends of the C-shaped handle. In one embodiment, the second anatomical alignment marker preferably comprises a projection adapted to engage a tail bone for aligning the lower end of the handle with the tail bone. In one embodiment, the projection may be a sacral spoon that desirably has a concave surface adapted to engage a bottom of a tail bone.

In one embodiment, the placement device preferably includes a pivoting arm having an upper end pivotally coupled with the upper end of the handle and a lower end adapted to pivot toward and away from the handle. In one embodiment, the pivoting arm is preferably adapted to pivot within a plane defined by a longitudinal axis of the handle. In one embodiment, the gate is desirably rotatably coupled with the lower end of the pivoting arm so that the gate is capable of swinging to the left and the right between the left and right sides of the handle.

In one embodiment, the gate is adapted to hold medical patches that are positioned on a patient's back. In one embodiment, the gate preferably comprises a first face and a first alignment ridge projecting from the first face, a second face and a second alignment ridge projecting from the second face, and a first opening extending through the gate between the first and second faces of the gate. The device preferably includes a flexible diaphragm disposed within the first gate opening. The flexible diaphragm desirably includes a flexible dome that is adapted to be selectively pressed through the first gate opening for selectively moving the dome between the first and second faces of the gate. In one embodiment, at least one magnet is located in a center of the flexible dome for holding a portion of a medical patch (e.g. a metallic portion) against the diaphragm.

In one embodiment, the first and second ridges on the swinging gate are desirably adapted to surround an outer perimeter of a medical patch when the medical patch is loaded on the gate. In one embodiment, at least one of the first and second ridges includes at least one slot adapted to receive at least one tab accessible at the outer perimeter of the medical patch.

In one embodiment, a placement device for positioning a medical patch on a patient includes a handle including a shaft having an upper end and a lower end. The upper end of the shaft desirably includes a first alignment marker adapted for alignment with a patient's spine and the lower end of the shaft desirably includes a second alignment marker adapted for alignment with the patient's tail bone. The placement device preferably includes a gate adapted to receive a medical patch, whereby the gate is both pivotally coupled with the upper end of the shaft for being selectively pivoted toward and away from the shaft and rotationally coupled with the upper end of the shaft for swinging the gate through an arc extending between opposite sides of the shaft.

In one embodiment, the placement device may include an adjustable spacer for selectively adjusting spacing between the gate and the upper and lower ends of the shaft. In one embodiment, the adjustable spacer preferably couples the gate with the upper end of the shaft. In one embodiment, a placement device may include a plurality of adjustable spacers having varying lengths for accommodating patients having different sizes or heights.

In one embodiment, the swinging gate preferably comprises a first major face, a second major face, and a first opening extending through the gate between the first and second major faces. The gate may include a flexible diaphragm disposed within the first gate opening, whereby the flexible diaphragm includes a flexible dome that is adapted to be selectively pressed through the first gate opening for transforming the shape of the flexible diaphragm between a concave cup facing the first face of the gate and a convex dome facing the first face of the gate. At least one magnet may be located in a center of the flexible dome for holding a medical patch within the flexible dome or against the flexible diaphragm.

In one embodiment, the gate desirably includes a first alignment ridge projecting from the first major face of the gate and a second alignment ridge projecting from the second major face of the gate. The first alignment ridge is desirably adapted to surround an outer perimeter of a medical patch when the medical patch is loaded onto the first major face of the gate and the second alignment ridge is desirably adapted to surround an outer perimeter of a medical patch when the medical patch is loaded onto the second major face of the gate. In one embodiment, at least one of the first and second ridges includes a slot adapted to receive a tab accessible at the outer perimeter of the medical patch.

In one embodiment, a placement device for enabling a patient to self-locate and position a medical patch on a patient's body includes an alignment guide including a C-shaped handle or shaft having a first end with a first anatomical alignment marker and a second end with a second anatomical alignment marker, and a swinging gate both pivotally and rotationally coupled with the first end of the shaft for selectively pivoting the swinging gate within a plane toward and away from the shaft and selectively rotating the swinging gate between opposite sides of the shaft. In one embodiment, the gate preferably includes a first major face, a second major face, and a first opening extending through the gate between the first and second major faces. The placement device desirably includes an adjustable spacer coupling the gate with the first end of the shaft for selectively adjusting spacing between the gate and the first end of the shaft, and a flexible diaphragm disposed within the first gate opening, whereby the flexible diaphragm includes a flexible dome that is adapted to be selectively pressed through the first gate opening for transforming the shape of the flexible diaphragm between a concave cup facing the first face of the gate and a convex dome facing the first face of the gate. The placement device desirably includes at least one magnet located in a center of the flexible dome for holding a medical patch within the flexible diaphragm.

In one embodiment, the swinging gate is preferably swung to the left of the shaft when it is desirably to place a medical patch on a left side of a patient and swung to the right of the shaft when it is desirable to place a medical patch on a right side of a patient. A single placement device may preferably be used for placing the medical patch on either side of the patient.

The medical patches that may be placed include medical patches having an active region that is adapted to deliver neurostimulation (e.g. a SNS patch), pain-management agents, hormones, or pharmacological agents to a target location on a patient.

In one embodiment, the placement device preferably includes a handle that is coupled with the swinging gate. In one embodiment, the handle may be used to provide tactile feedback that the placement device is properly aligned with the spine, thereby providing lateral positioning. In one embodiment, the placement device is preferably designed to be portable so that a patient may easily transport it outside the home.

In one embodiment, the placement device provides a tool that enables a patient to consistently and accurately place a series of medical patches over a target location on a patient. In one embodiment, replacement patches are preferably placed on the body by patients at home, and the placement device will desirably serve to ensure both accuracy of placement and consistency of placement over one or more target locations.

In one embodiment, a medical patch may be constructed from well-known electrode materials such as silver, silver/silver chloride, gold, titanium, or other conductive materials. The medical patch may also be made of conductive polymers, fibers and the like. The medical patch may be a standalone component as described in commonly owned U.S. patent application Ser. No. 11/146,522, the disclosure of which is hereby incorporated by reference herein. In instances where the medical patch is incorporated into a flexible circuit, the flexible circuit may contain all of the required electronics required for generating stimulation signals. The flexible circuit may include mounting regions for receiving battery cells.

In one embodiment of the present invention, a placement device is used for accurately and consistently placing one or more medical patches over a specific target location on a body. In one embodiment, the placement device is preferably adapted to use one or more anatomical landmarks on a patient's body to precisely place the medical patch over a target location. In one embodiment, the placement device preferably includes a handle having an upper section, a curved shaft, and a lower section having a spoon-like cup, and a swinging gate adapted to hold a medical patch and accurately position the patch over the target location.

In one embodiment, the handle of the placement device is preferably adapted to be easily and comfortably held in either hand of a patient. In one embodiment, the handle is shaped like a "C" so that it may be used comfortably and may accommodate differences in anatomical shapes of the buttocks. In one embodiment, the placement device includes one or more vertical adjustment elements for accommodating patients having different heights. In one embodiment, the upper end of the handle preferably has an outwardly curved portion is used to provide tactile feedback to the patient that the placement device is properly lined up with a preferred anatomical feature on the body, thereby providing accurate lateral positioning. In one embodiment, the preferred anatomical feature is the patient's spine.

In one embodiment, the placement device preferably includes a cup that is attachable to the bottom portion of the handle. The cup is preferably a spoon shaped device adapted to fit comfortably under the distal end of the sacrum at the point where the coccyx begins and curves inward (sacrococcygeal junction or tailbone), which desirably helps provide for accurate placement of the medical patch. The shape of the cup is preferably adapted for placement through the gluteal cleft and under the sacrococcygeal junction. The cup is desirably curved for ergonomic reasons so that it fits comfortably, and is made from a soft but sturdy material. The dimensions or orientation of the cup may be adjustable to accommodate patients having varying body types.

In one embodiment of the present invention, the components overlying the substrate include a power source, such as a battery, and a switch coupled with the power source for activating the patch. The switch may be a single-use switch that is adapted to be activated only one-time. The components may also include a light emitting element, such as an LED, for generating light signals indicating that the patch is activated, and an optical sensor, such as a photodiode, adapted to receive signals for controlling parameters associated with the at least one nerve stimulating signal. In one embodiment, a remote control may be used for directing light signals at the photodiode, and the detected light signals are used to adjust the nerve stimulating output of the patch. In one embodiment, the switch to activate the medical patch may be a photodiode. In one embodiment, when the medical patch is activated, an optical transceiver may be used for providing two-way communication between the medical patch and the remote control or controller. The transceiver may include a LED to transmit information to the controller and a receiver that desirably receives commands from the controller.

In one embodiment of the present invention, a nerve stimulation patch includes a circuitized substrate having a top surface and a bottom surface, a plurality of integrated components overlying the top surface of the circuitized substrate for generating at least one nerve stimulating signal, a power source overlying the top surface of the circuitized substrate for energizing the integrated components, and electrodes disposed within the circuitized substrate. The electrodes are accessible at the bottom surface of the circuitized substrate, and are electrically interconnected with the integrated components for applying the at least one nerve stimulating signal. The selective nerve stimulation patch desirably includes a waterproof, breathable cover overlying the circuitized substrate, and a support flange coupled with and surrounding the circuitized substrate, the support flange having a top surface that slopes downwardly toward an outer perimeter thereof. The support flange may be flexible and may have a plurality of vent openings accessible at the sloping top surface thereof that are in communication with the waterproof, breathable top cover for venting moisture from the patch.

In one embodiment, the nerve stimulation patch includes conductive, adhesive pads, such as adhesive hydrogel pads, overlying the electrodes for securing the patch to a surface. The conductive, adhesive pads are replaceable, which enables the patch to be temporarily removed from a surface and then replaced or re-positioned on the surface.

In one embodiment of the present invention, a transparent encapsulant material overlies the integrated components, and the support flange surrounds the transparent encapsulant. The integrated components may include a power source, a one-time activation switch (e.g. a photodiode), a light emitting element, and an optical sensor (e.g. a transceiver system including a light emitting element and an optical sensor). In one embodiment, the waterproof, breathable cover has a first opening aligned with the one-time activation switch, a second opening aligned with the light emitting element, and a third opening aligned with the optical sensor. The patch may include conductive, adhesive pads covering the electrodes, and an adhesive layer covering a peripheral, underside portion of the waterproof, breathable cover for attaching the patch to a surface. The adhesive pads and the adhesive layer may enable the patch to be temporarily removed from a surface, and then later re-attached to the surface. In one embodiment, the adhesive pads may be replaced with new adhesive pads.

In one embodiment of the present invention, the selective nerve stimulation patch may include one or more electrodes, one or more waveform generators, one or more modulators, and a battery. The waveform generators preferably generate waveforms capable of selectively stimulating target nerves and penetrating the tissues between the patch and the target nerves. A battery is a preferred power source for the nerve stimulation patch, and the waveform generators draw power from the battery. The modulator modulates the waveforms from the waveform generator to produce a modulated waveform, and sends it to the electrodes. Upon receiving the electrical signals from the modulator, the electrodes desirably generate an electric field for stimulating the target nerve.

In one embodiment of the present invention, the battery is a non-rechargeable battery. In another embodiment of the present invention, the battery is a rechargeable battery, which may be recharged using a radio frequency signal, by using inductive coupling to transfer energy through a shared magnetic field, or by using any other known technique for recharging power sources.

In one or more embodiments of the present invention, the selective nerve stimulation patch is adapted to generate a modulated waveform for stimulating a target nerve using the devices and techniques described in commonly assigned United States Patent Application Publication Nos. US 2005/0277998 (U.S. application Ser. No. 11/146,522, filed Jun. 7, 2005), and US 2006/0195153 (U.S. application Ser. No. 11/343,627, filed Jan. 31, 2006), the disclosures of which are hereby incorporated by reference herein. The waveform is desirably generated by modulating a carrier waveform with a pulse envelope. Properties of the carrier waveform such as amplitude, frequency, and the like, are chosen so as to overcome the tissue impedance and the stimulation threshold of the target nerve. The pulse envelope is a waveform having a specific pulse width, amplitude and shape designed to selectively stimulate the target nerve. This waveform is able to penetrate efficiently through the tissue to reach the target nerve with minimal loss in the strength of the electrical signal, thereby saving battery power that would otherwise have been used in several attempts to stimulate the target nerve with low frequency signals. Moreover, only the target nerve is stimulated, and non-target nerves are not stimulated.

Although one or more embodiments of the present invention are described in relation to nerve stimulation in females and the female urinary system, it is to be understood that the present invention may be readily adapted for nerve stimulation in males, children, and adults, and use in the urinary system or males, children, and adults. Further, the inventive principles, apparatus and methods disclosed herein may also have application to assessing and treating functionality in other areas, such as coronary or pulmonary functionality. Still further, the inventive principles, apparatus and methods disclosed herein may have application for stimulating various other nerves, such as stimulation of nerves during labor and delivery, or selectively stimulating branches of a given nerve bundle to selectively address different patient conditions. In addition, the technology described herein can be applied to various components of the nervous system that contribute or affect the following conditions: stress urinary incontinence, anal and fecal incontinence, sexual dysfunction, interstitial cystitis, chronic pain such as but not limited to pelvic pain, nocturia, and gastrointestinal disorders such as but not limited to gastric pacing. Moreover, the present invention may be used to stimulate body parts other than nerves, such as glands that secrete hormones, and large muscle groups, such as biceps muscle stimulation associate with physical therapy.

These and other preferred embodiments of the present invention will be described in more detail below.

BRIEF DESCRIPTION OF THE DRAWING

FIG. 1 shows an exploded view of a placement device for a medical patch including a handle, a sacral cup, a pivoting arm, a spacer, a swinging gate, and a flexible diaphragm, in accordance with one embodiment of the present invention.

FIG. 3 shows a perspective view of the handle shown in FIG. 1.

FIG. 4 shows a perspective view of the sacral cup shown in FIG. 1.

DETAILED DESCRIPTION

Figure 2A:
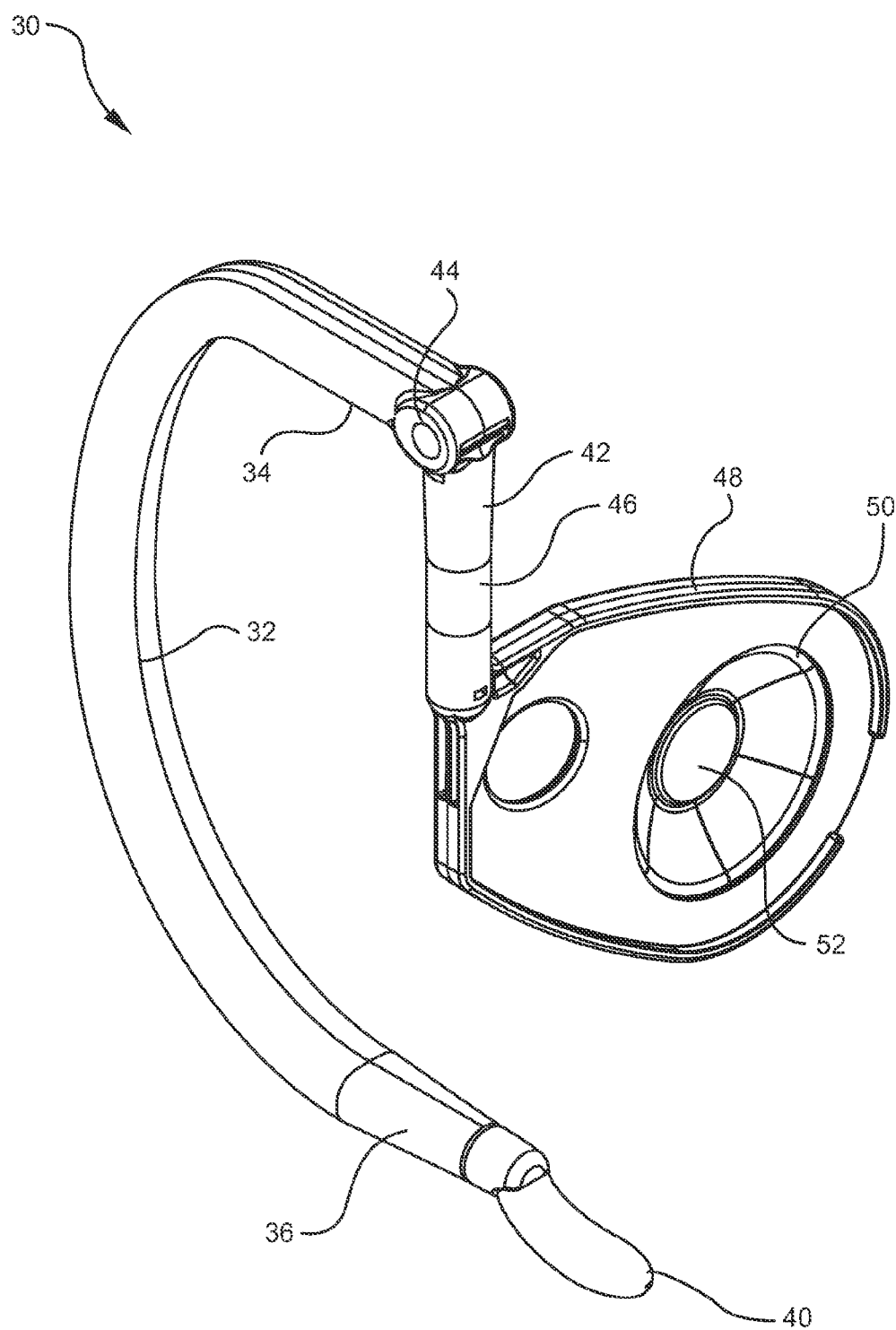
FIGS. 2A-2D show a placement device for a medical patch, in accordance with one embodiment if the present invention.

FIG. 1 shows an exploded view of a placement device 30 that is utilized for accurately positioning one or more medical patches on a patient for maximizing therapeutic benefit to the patient, in accordance with one embodiment of the present invention. In one embodiment, the placement device 30 is desirably bilateral so that it may be used for alternatively positioning a medical patch on either the right side or the left side of a patient, such as on the right or left side of a patient's back. In one embodiment, the placement device 30 preferably includes a handle 32 having an upper end 34, a lower end 36 and a shaft 38 extending between the upper and lower ends. In one embodiment, the shaft 38 may be C-shaped. The placement device 30 preferably includes a sacral cup 40 extending from the lower end 36 of the handle 32. In one embodiment, the sacral cup may be a separate part that is secured to the lower end of the handle. In one embodiment, the sacral cup may be integrally formed with the lower end 36 of the handle 32.

In one embodiment, the placement device preferably includes a pivoting arm 42 having an upper end that is pivotally coupled with the upper end 34 of the handle 32 via one or more pivot shafts 44A, 44B. In one embodiment, the pivot shafts 44A, 44B are preferably coupled with a pair of aligned openings 45A, 45B provided at the upper end 34 of the handle. The pivot shafts may be snap-fit into the aligned openings 45A, 45B. In one embodiment, the pivoting arm is preferably adapted for pivoting toward and away from the handle within a plane defined by the longitudinal axis of the handle.

In one embodiment, the placement device 30 preferably includes a spacer 46 that may have an upper end coupled with a lower end of the pivoting arm 42. The length of the spacer 46 may vary depending upon the size of the patient. In one embodiment, the placement device may have a plurality of spacers 46 having various lengths for modifying the device for use on patients having various sizes and/or heights.

Referring to FIG. 1, in one embodiment, a lower end of the pivoting arm 42 is adapted to receive an upper end of the spacer 46. An O-ring 54 may be positioned between the upper end of the spacer 46 and the opening at the lower end of the pivoting arm 42 for forming a secure connection between the spacer 46 and the pivoting arm 42.

In one embodiment, the spacer 46 preferably has a lower end that is adapted to fit into an opening, such as a shaft opening, provided at an upper end of a swinging gate 48. As will be described in more detail herein, the swinging gate 48 is desirably adapted to both hold a medical patch and swing to the left or the right for positioning the medical patch on the left or right side of a patient. In one embodiment, the swinging gate 48 preferably includes a larger opening 56 and a smaller opening 58. The larger opening 56 of the gate 48 is adapted to receive and seat a flexible diaphragm 50, which is held in the larger opening 56 by a retaining ring 60. The placement device 30 also preferably includes the magnet assembly 52 that is adapted to be positioned at the center of the flexible diaphragm 50. In one embodiment, the magnet assembly 52 preferably includes a magnet holder 62 that is desirably adapted to hold a pair of magnets 64A, 64B. In one embodiment, the magnet holder 62 holds the first magnet 64A on a first face of the flexible diaphragm 50 and a second magnet 64B on the second face of the flexible diaphragm 50.

In one embodiment, the gate 48 preferably extends along a longitudinal axis that forms an angle of between about 20-45° and more preferably about 30° when assembled with the lower end of the spacer 46. In one embodiment, a spacer may not be used and the gate 48 may be directly coupled with the lower end of the pivoting arm 42. In one embodiment, the handle 32 may be a molded part. In one embodiment, the handle 32 is preferably made of a Delrin® material that is about 25% filled with glass. The sacral cup 40 may be made of a combination of a Delrin® material without a glass filling and a santoprene material. In one embodiment, the spacer 46 may be made of a Delrin® material without a glass filling. The flexible diaphragm 50 may be made of a silicone material.

Figure 2B:
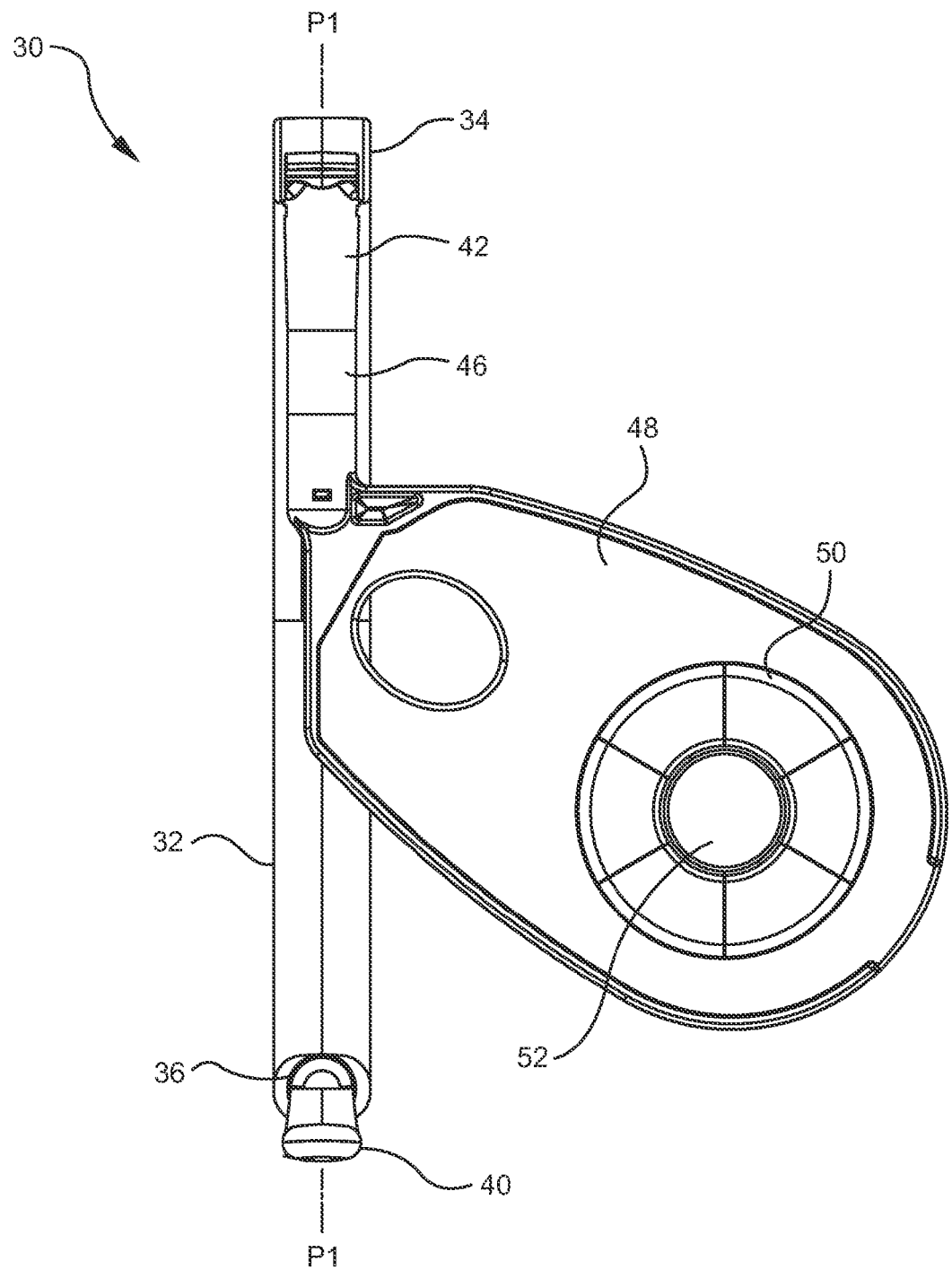

Referring to FIGS. 1 and 2A, in one embodiment, the swinging gate 48 is preferably secured to a lower end of the spacer 46, which, in turn, is coupled with a lower end of the pivoting arm 42. Referring to FIG. 2B, in one embodiment, the handle has a longitudinal axis that lies in a plane $P_1$ and the pivoting arm 42 and spacer 46 are aligned with and pivot within the plane $P_1$.

Figure 2C:
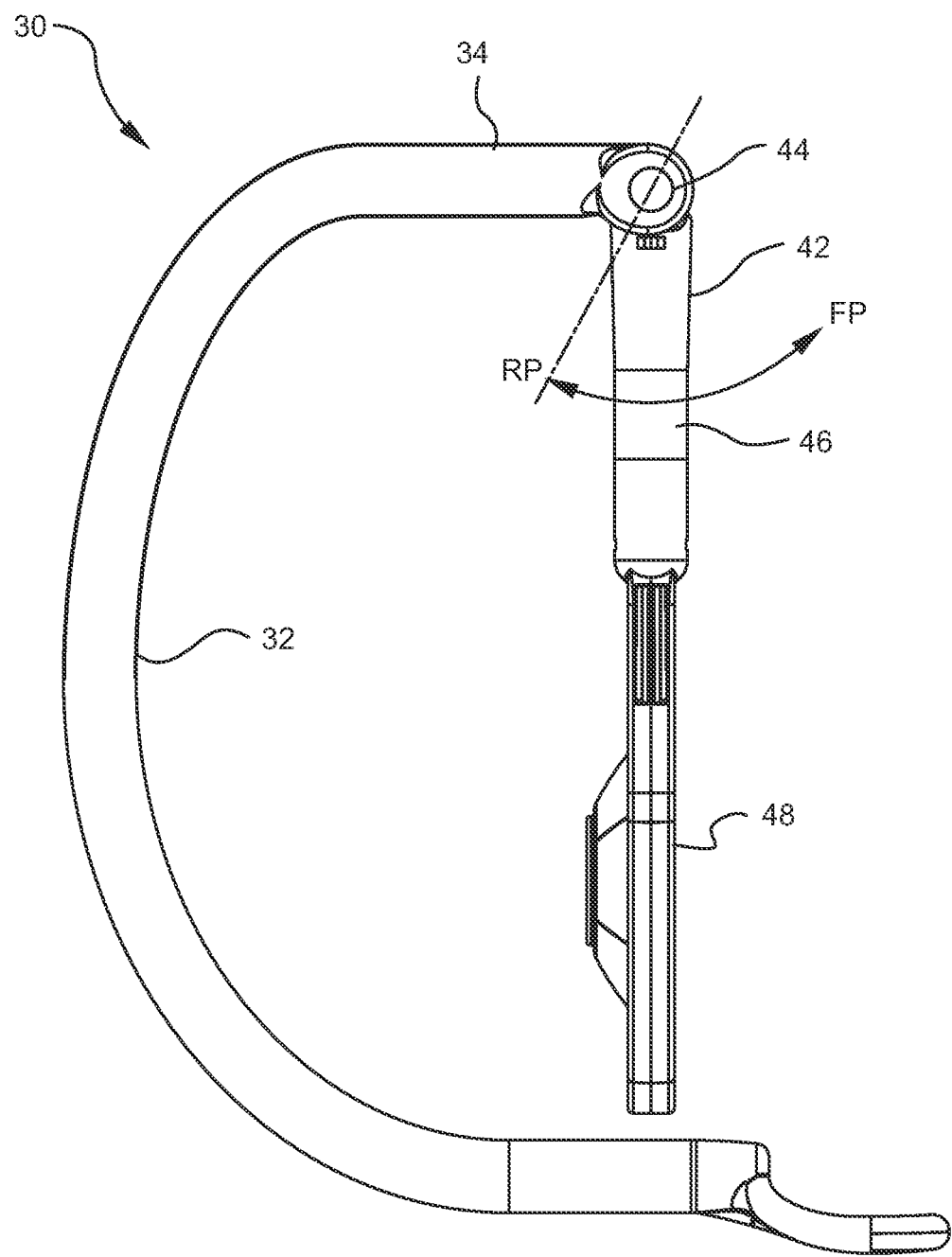

Referring to FIGS. 2B and 2C, in one embodiment, the upper end of the pivoting arm 42 is pivotally coupled with the upper end 34 of the handle 32. In one embodiment, the pivoting arm 42 is adapted to pivot about pivot shaft 44 so that the lower end of the pivot arm is movable along the arc designated RP-FP, as shown in FIG. 2C. In one embodiment, the pivoting arm 42 is able to pivot away from the handle 32 (within the plane $P_1$ shown in FIG. 2B) to the point designated FP. The pivoting arm 42 is also able to pivot toward the handle 32 to the point designated RP. The placement device 30 desirably includes a stop that limits forward and rearward pivoting of the pivoting arm 42. As noted above, as the pivoting arm 42 pivots forward and rearward, the pivoting arm and the spacer 46 preferably remain within the plane $P_1$ shown in FIG. 2B. Although the present invention is not limited by any particular theory of operation, it is believed that the forward and rearward pivoting capabilities of the pivoting arm 42 enable the placement device to be easily used on patient's having different sizes. For example, a larger patient having a larger posterior would require greater rearward movement of the pivoting arm 42 for accommodating the greater dimensions of the patient. A smaller patient having a smaller posterior would require less rearward movement of the pivoting arm.

Figure 2D:
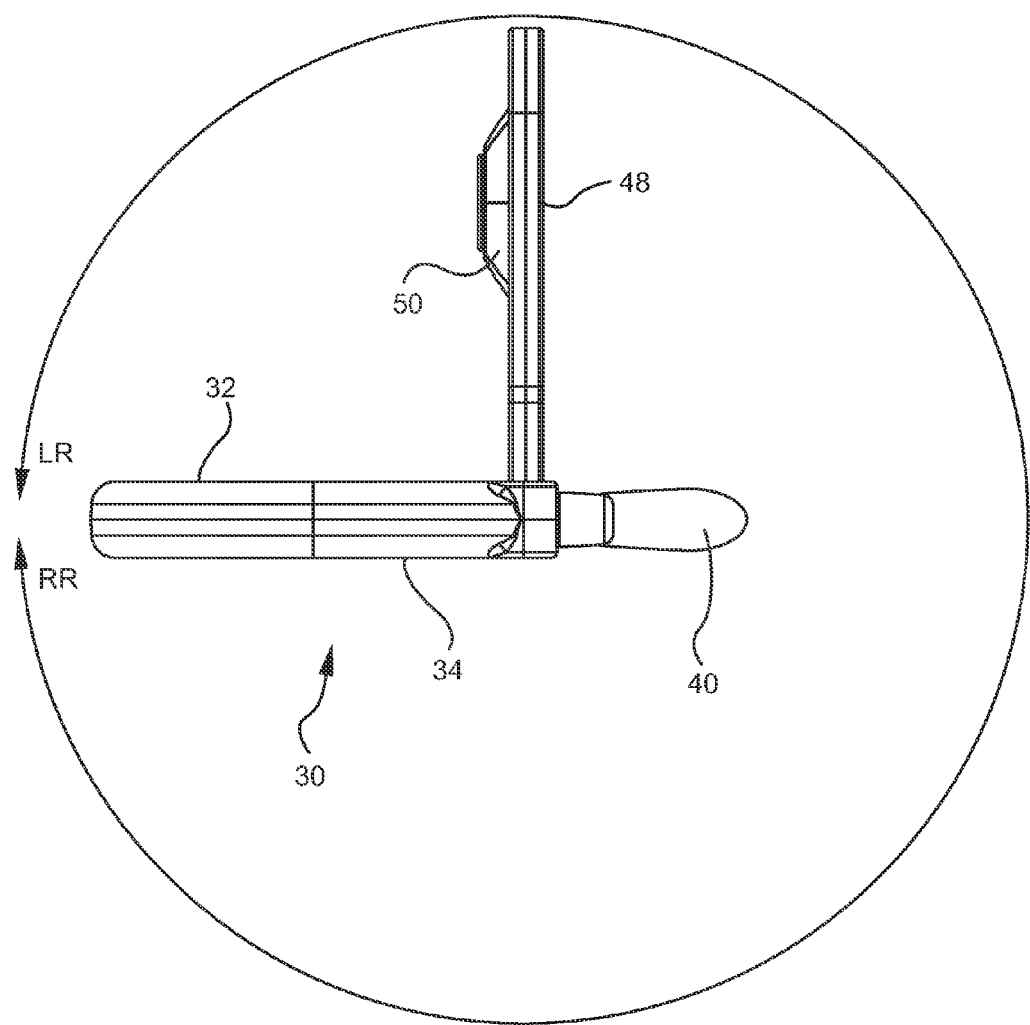

Referring to FIGS. 2A-2D, in one embodiment, the gate 48 is a swinging gate that is attached to a lower end of the spacer. In one embodiment, the gate 48 is preferably adapted to swing about a longitudinal axis of the spacer 46. Referring to FIG. 2D, in one embodiment, the gate 48 is free to swing from at least 90 degrees left to at least 90 degrees right, and more preferably from about 170 degrees left to about 170 degrees right. In FIG. 2D, the maximum left range of the gate 48 is designated LR, and the maximum right range of the gate 48 is designated RR. In one embodiment, the swinging gate 48 preferably swings to the left until the gate physically contacts the left side of the handle, and to the right until the gate physically contacts the right side of the handle. In one embodiment, the placement device including the swinging gate preferably provides for bilateral positioning of medical patches on either on the left side or the right side of a patient. In the particular configuration shown in FIG. 2D, the placement device 30 is in position for placing a medical patch on a left side of a patient. The gate 48 may be swung to the right side of the handle 32 for positioning a medical patch on the right side of the patient.

Referring to FIG. 3, in one embodiment, a handle 32 for a placement device includes an upper end 34, a lower end 36 and a C-shaped shaft 38 extending therebetween. In one embodiment, the handle 32 includes two molded halves 70A, 70B that are desirably snap-fit together. The handle 32 is preferably made of durable materials such as polymers.

In one embodiment, the upper end 34 of the handle 32 extends along an axis designated $A_1$ and the lower end 36 of the handle extends along a second axis designated $A_2$, whereby the first and second axes $A_1$, $A_2$ extend in planes that are substantially parallel with one another.

In one embodiment, the upper end 34 of the handle 32 includes a pair of aligned openings 45A, 45B that are adapted to receive one or more pivot shafts 44A, 44B provided at the upper end of the pivoting arm (FIG. 1). In one embodiment, the lower end 36 of the handle 32 has an opening 74 formed at a leading end thereof. In one embodiment, the opening 74 is preferably a cruciform-shaped opening 76 adapted to receive a trailing shaft of a sacral cup, as will be described in more detail below.

Referring to FIG. 4, in one embodiment, the placement device includes a sacral cup 40 having a leading end 80 and a trailing end 82. The sacral cup 40 includes a spoon 84 having a concave-shaped top surface 86 adapted to engage a bottom of a patient's tail bone. The spoon 84 includes a stop 88 that preferably extends upwardly from a trailing end of the concave surface 86. The stop 88 is adapted to prevent further advancement of the sacral cup after the spoon 84 has been abutted against the patient's tail bone. The sacral cup 40 also preferably includes a trailing shaft 90 adapted for insertion into the opening 74 (FIG. 3) at the lower end 36 of the handle 32 for connecting the sacral cup with the lower end of the handle. In one embodiment, the shaft 90 has a cruciform-shape that is adapted to engage the cruciform shaped opening 76 at the lower end 36 of the handle 32.

Figure 5A:
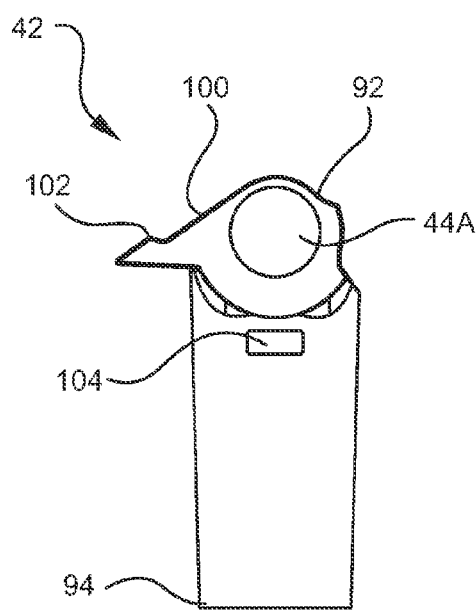
FIGS. 5A-5C show respective side elevational, front perspective, and top plan views of the pivoting arm shown in FIG. 1.
Figure 5B:
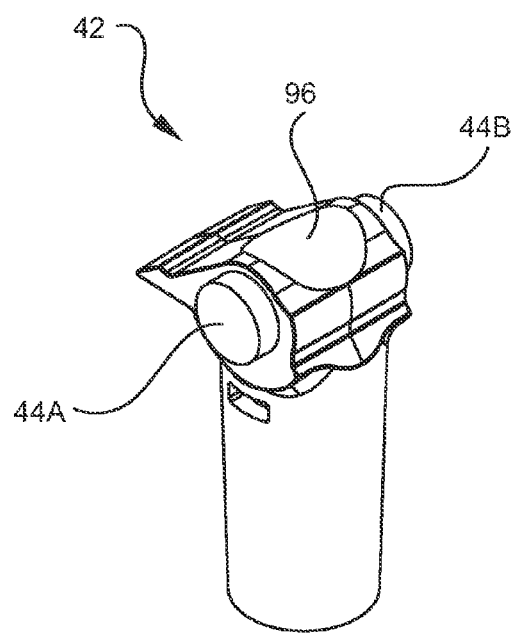
Figure 5C:
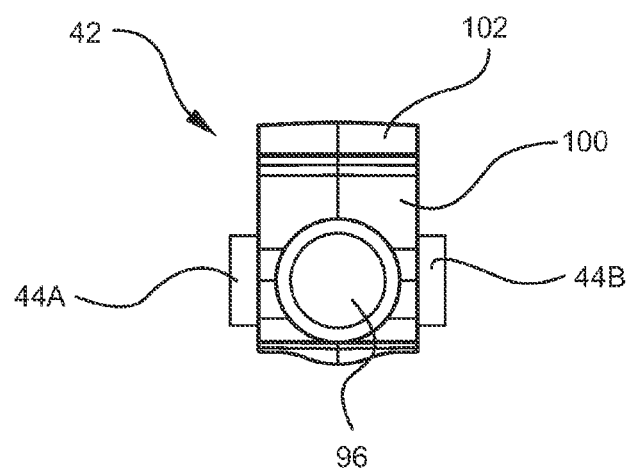

Referring to FIGS. 5A-5C, in one embodiment, a medical patch placement device desirably includes a pivoting arm 42. In one embodiment, the pivoting arm 42 includes an upper end 92, a lower end 94, and a central opening 96 extending between the upper end 92 and the lower end 94. Referring to FIG. 5A, in one embodiment, the pivoting arm 42 includes a pair of aligned slits 104 that are adapted to receive coupling teeth provided on a spacer, as will be described in more detail below.

In one embodiment, the pivoting arm 42 preferably includes a first pivot shaft 44A projecting from one side of the pivoting arm and a second pivot shaft 44B projecting from an opposite side of the pivoting arm. The first and second pivot shafts 44A, 44B are preferably in substantial alignment with one another. Referring to FIGS. 3 and 5B, in one embodiment, the pair of pivot shafts 44A, 44B are adapted to be inserted into the respective openings 45A, 45B at the upper end 34 of the handle 32 (FIG. 3) so that the pivoting arm 42 is pivotally connected with the upper end 34 of the handle 32. The pivoting arm 42 also desirably includes a sloping surface 100 that slopes in a downward direction toward a trailing end of the pivoting arm 42. The sloping surface 100 desirably extends to a pivot stop 102 that limits the range of rearward pivoting of the pivoting arm 42 toward the handle.

Figure 6A:
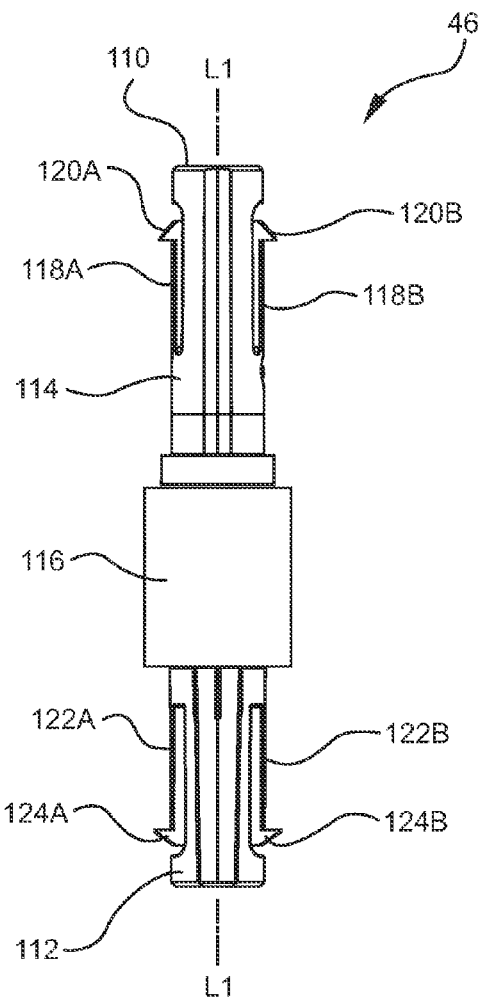
FIGS. 6A and 6B show respective side elevational and perspective views of the spacer shown in FIG. 1.
Figure 6B:
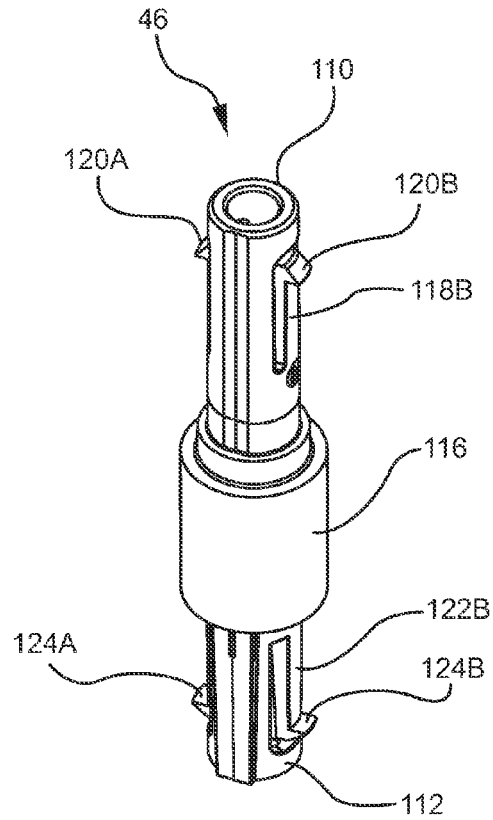

Referring to FIGS. 6A and 6B, in one embodiment, a placement device for a medical patch includes a spacer 46 having an upper end 110, a lower end 112, and an elongated shaft 114 extending between the upper and lower ends. In one embodiment, the elongated shaft 114 preferably extends between the upper and lower ends along a longitudinal axis designated $L_1$. The spacer 46 preferably includes a cylindrical-shaped central section 116 having an outer surface having a larger diameter than the diameter of the elongated shaft 114.

In one embodiment, the upper end of the spacer 42 includes a pair of upper coupling arms 118A, 118B having respective teeth 120A, 120B. In one embodiment, the upper end 110 of the shaft 114 of the spacer 46 is insertable into the central opening 96 (FIG. 5C) extending through the pivoting arm 42. The upper end 110 of the shaft 114 is preferably advanced into the central opening 96 of the pivoting arm until the teeth 120A, 120B of the coupling arms 118A, 118B snap-fit into the aligned slits 104 (FIG. 5A) for coupling the spacer 46 with the pivoting arm 42.

In one embodiment, the lower end 112 of the spacer 46 desirably includes flexible lower coupling arms 122A, 122B having respective coupling teeth 124A, 124B. As will be described in more detail below, the lower end 112 of the shaft 114 is adapted to be inserted into an opening provided at an upper end of a swinging gate. The teeth 142A, 142B are adapted to be snap-fit into slits provided in the gate.

Figure 7A:
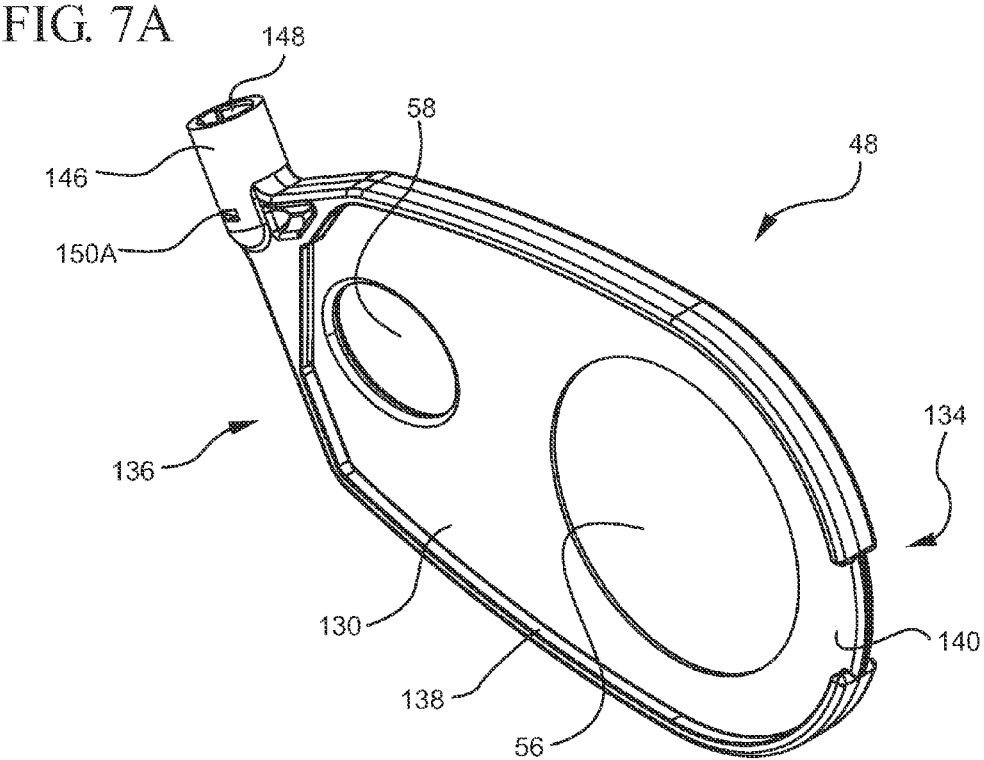
FIG. 7A shows a perspective view of a first face of the swinging gate shown in FIG. 1.
Figure 7B:
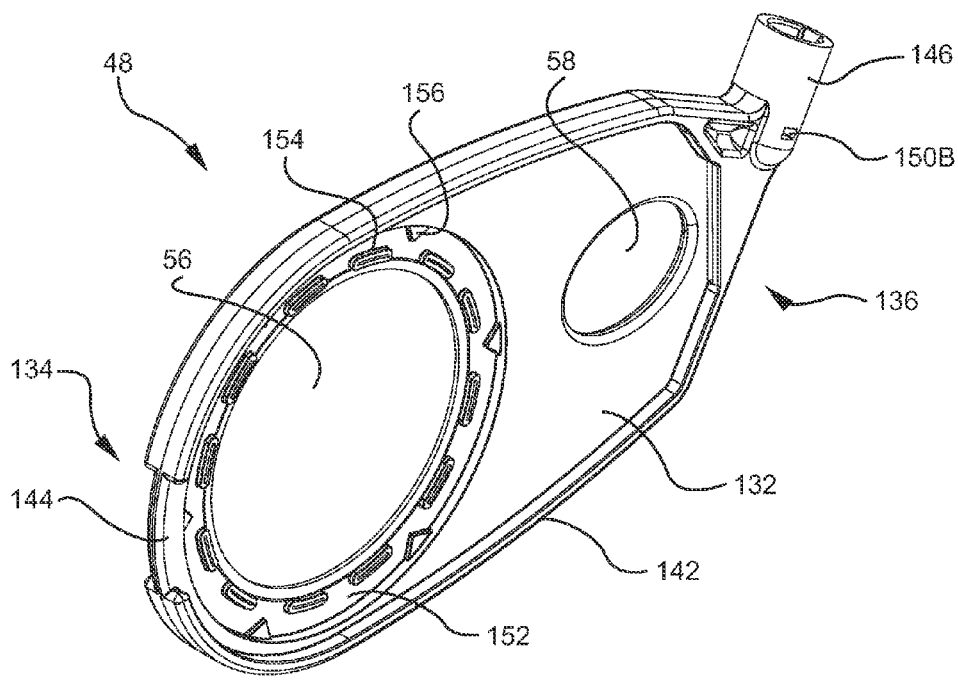
FIG. 7B shows a perspective view of a second face of the swinging gate shown in FIG. 1.

Referring to FIGS. 7A and 7B, in one embodiment, a swinging gate 48 for a medical patch placement device preferably includes a larger opening 56 and a smaller opening 58. The gate 48 preferably includes a leading end 134, and a trailing end 136 that is preferably attached to a lower end of the spacer 46 shown in FIGS. 6A and 6B. FIG. 7A shows a perspective view of a first face 130 of the swinging gate 48 and FIG. 7B shows a perspective view of a second face 132 of the swinging gate 48. The first face 130 of the gate 48 has an outer perimeter, and a first ridge 138 that projects above the first face 130 and extends around the outer perimeter of the first face. The first ridge is preferably adapted to surround the outer perimeter of a medical patch loaded onto the first face of the gate for holding the patch in place. The first ridge 138 preferably has a tab alignment opening 140 provided at the leading end 134 of the gate 48.

Referring to FIG. 7B, in one embodiment, the swinging gate 48 preferably has a second face 132 having an outer perimeter, and the gate 48 includes a second ridge 142 that extends above the second face 132 and surrounds the outer perimeter of the second gate. The second ridge is preferably adapted to surround the outer perimeter of a medical patch loaded onto the second face of the gate for holding the patch in place. The second ridge 142 desirably includes a tab alignment opening 144 provided at the leading end 134 of the gate 48.

Referring to FIGS. 7A and 7B, in one embodiment, the trailing end 136 of the gate 48 has a shaft 146 projecting upwardly therefrom. The shaft 146 desirably has an opening 148 adapted to receive the lower end 112 of the spacer 46 (FIG. 6A). The shaft 146 also preferably includes aligned slits 150A, 150B that are adapted to receive the respective teeth 124A, 124B provided on the arms 122A, 122B at the lower end 112 of the spacer 46 (FIG. 6A). After the opening 148 of the shaft 146 of the gate is coupled with the spacer shaft 114, the gate shaft 146 is adapted to rotate about the longitudinal axis $L_1$ of the spacer 46.

Referring to FIG. 7B, in one embodiment, the second face 132 of the swinging gate 48 desirably includes an annular depression 152 formed therein that is adapted to receive a peripheral portion of the flexible diaphragm 50 (FIG. 1). Alignment elements 154, 156 are desirably provided within the annular depression 152. The alignment elements 154, 156 are preferably projecting elements that engage openings or notches formed in the outer periphery of the flexible diaphragm for aligning and holding the flexible diaphragm within the annular depression 152.

Figure 8A:
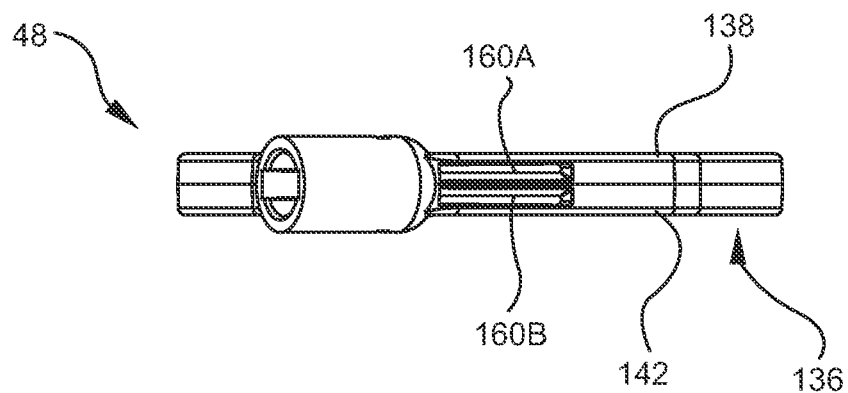
FIG. 8A shows a trailing end view of the swinging gate shown in FIG. 1.
Figure 8B:
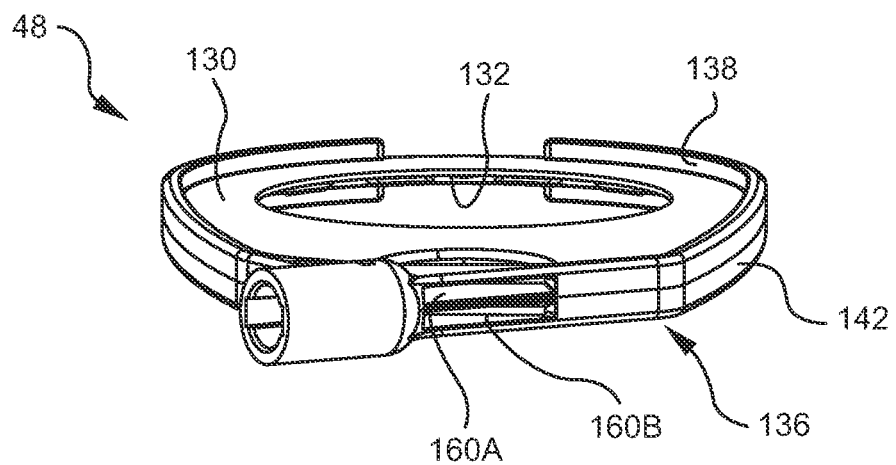
FIG. 8B shows a perspective view of the trailing end of the swinging gate shown in FIG. 8A.

Referring to FIGS. 8A and 8B, in one embodiment, the trailing end 136 of the swinging gate 48 preferably has a pair of tab alignment slits 160A, 160B formed therein. In one embodiment, the gate 48 desirably includes the first alignment ridge 138 projecting above the first face 130 of gate 48 and the second alignment ridge 142 projecting above the second face 132 of the gate 48. The first and second alignment ridges 138, 142 desirably include the tab alignment slits 160A, 160B, respectively, that are preferably adapted to receive tabs projecting from a trailing end of a medical patch, as will be described in more detail below. The first tab alignment slit 160A is preferably substantially aligned with the first face 130 of the gate 48 and the second tab alignment slit is preferably substantially aligned with the second face 132 of the gate.

Figure 9A:
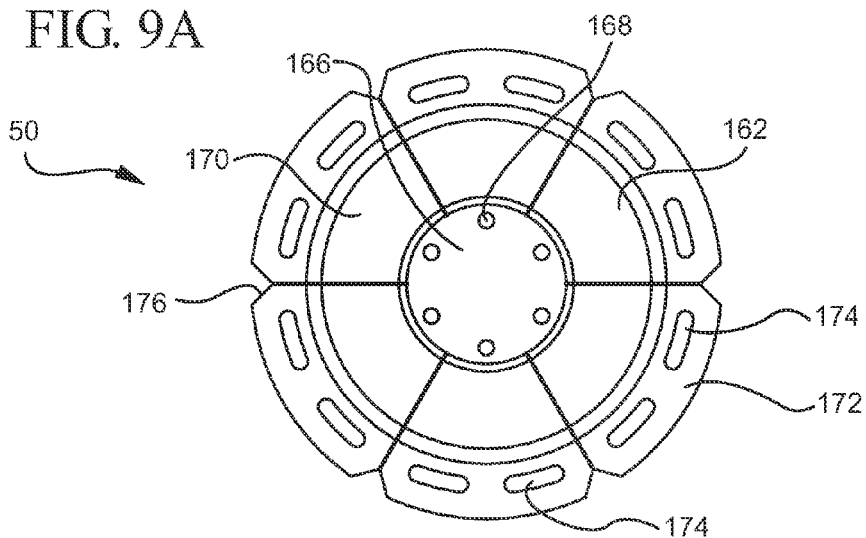
FIGS. 9A-9C show a flexible diaphragm adapted to engage a medical patch, in accordance with one embodiment of the present invention.
Figure 9B:
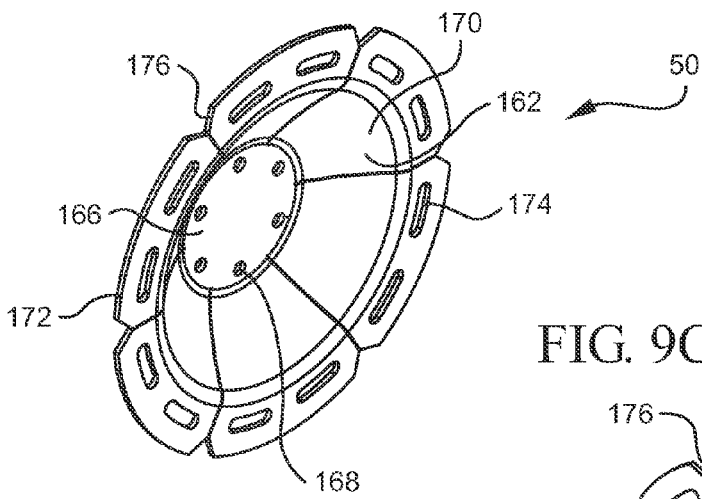
Figure 9C:
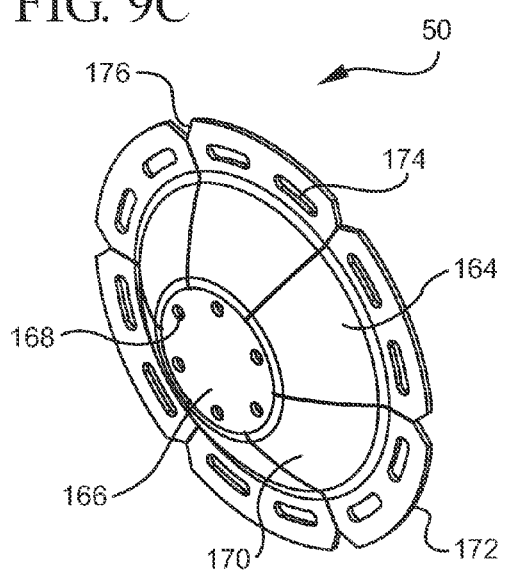

Referring to FIGS. 9A-9C, in one embodiment, a flexible diaphragm 50 for a medical patch placement device preferably includes a first face 162 (FIGS. 9A and 9B) and an opposing second face 164 (FIG. 9C). The flexible diaphragm 50 includes a central region 166 having a series of magnet holder openings 168 formed therein. In one embodiment, the central region 166 is preferably substantially flat, and the magnet holder openings 168 are adapted to receive projections provided on a magnet holder 62 (FIG. 1). The flexible diaphragm also desirably includes a flexible dome-shaped region 170 that surrounds the central region 166 thereof. In one embodiment, the flexible diaphragm is preferably made from a sheet of silicone that is cut to produce the dome shape. In one embodiment, the design of the silicone sheet preferably forms the dome and allows the dome to be invertible from a concave shape to a convex shape by pressing on the dome. The flexible diaphragm 50 also desirably includes a peripheral region 172 that surrounds the dome-shaped region 170. The peripheral region 172 desirably includes a plurality of elongated openings 174 that are adapted to engage the elongated projections 154 (FIG. 7B) on the second face 132 of the gate 48. The peripheral region 172 also desirably includes a plurality of V-shaped alignment grooves or notches 176 that are adapted to engage the triangular-shaped projections 156 projecting from the second face 132 of the swinging gate 48 (FIG. 7B).

In one embodiment, the flexible dome-shaped region 162 of the diaphragm 50 is adapted to be selectively transformable from the concave configuration shown in FIG. 9B to the convex configuration shown in FIG. 9C. In one embodiment, the flexible diaphragm 50 is transformed into the concave configuration of FIG. 9B so that the placement device may be used for positioning a medical patch on a right side of a patient. In one embodiment, the flexible diaphragm 50 may be transformed into the convex configuration shown in FIG. 9C so that the placement device may be utilized for positioning a medical patch on a left side of a patient, as will described in more detail below.

Figure 10A:
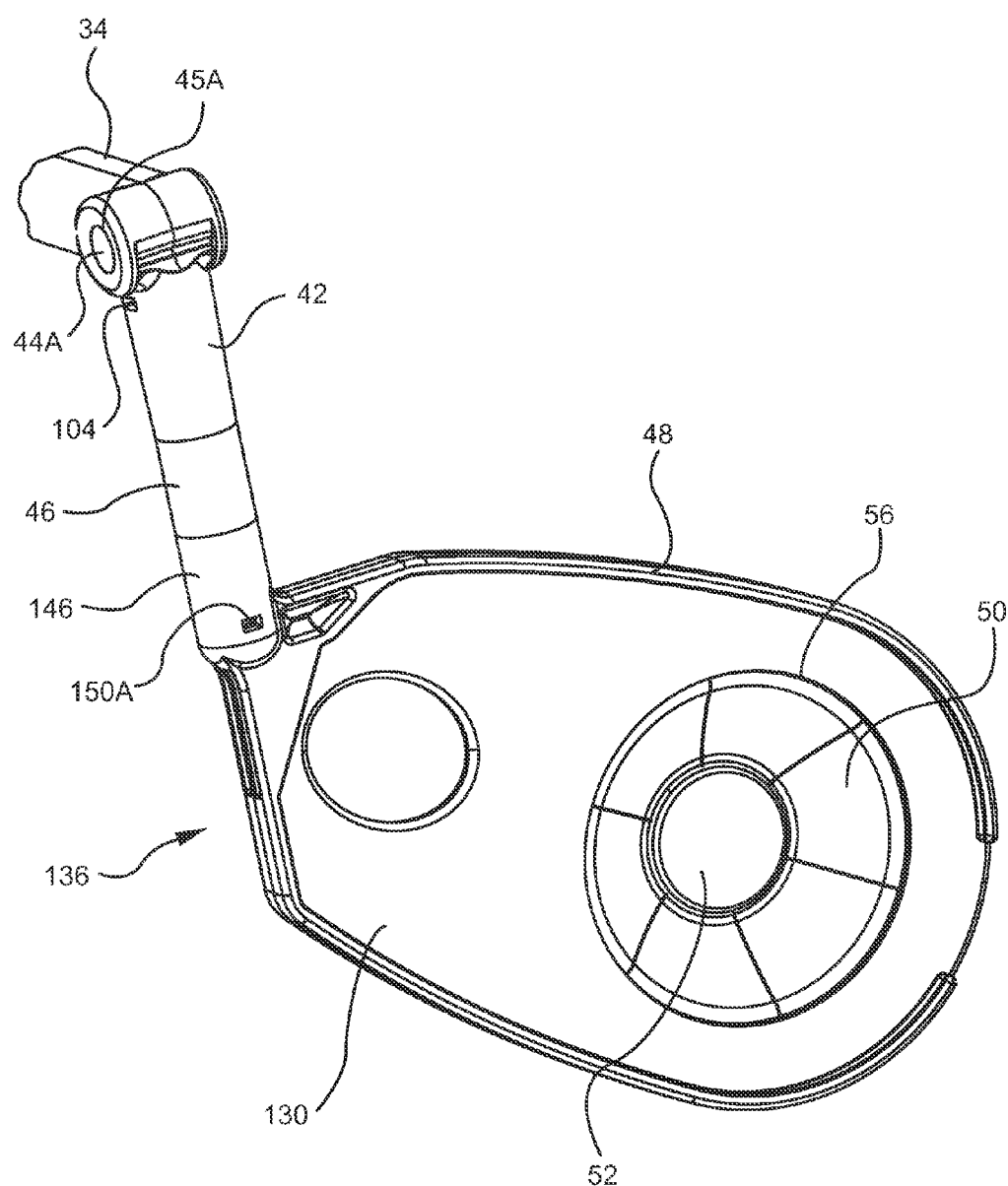
FIG. 10A shows a perspective view of a first face of the swinging gate of FIG. 1 after the flexible diaphragm of FIGS. 9A-9C has been assembled therewith, in accordance with one embodiment of the present invention.

Referring to FIG. 10A, in one embodiment, the swinging gate 48 includes the shaft 146 projecting upwardly from a trailing end 136 thereof. The shaft 146 is desirably coupled with a lower end of the spacer 46 so that the teeth 124A, 124B at the lower end of the spacer (FIG. 6A) snap-fit into the slots 150A, 150B provided in the shaft 146. In turn, the upper end of the spacer 46 may be coupled with the lower end of the pivoting arm 42 by snap fitting the attachment teeth 120A, 120B at the upper end 110 of the spacer 46 (FIG. 6A) into the slits 104 provided in the pivoting arm 42 (FIG. 5A). In turn, the pivot shafts 44A, 44B provided at the upper end of the pivoting arm 42 are snap fit into the aligned openings 45A, 45B provided at the leading end of the upper end 34 of the handle (FIG. 1).

As noted above, after the swinging gate 48 has been coupled with the upper end 34 of the handle, the pivoting arm 42 is preferably adapted to pivot toward and away from the shaft 38 of the handle 32 within a plane designated $P_1$ (FIG. 2B). The shaft 146 of the gate 48 is adapted to rotate about longitudinal axis $L_1$ of the spacer 46. The gate 48 is adapted to swing to the left until the gate engages a first or left side of the C-shaped shaft 38 of the handle 32, and to the right until the gate engages the second or right side of the C-shaped shaft section 38 of the handle 32. In one embodiment, the gate is able to swing between the left side and the right side by using a minimal amount of force to move the gate. The O-ring 54 (FIG. 1) between the bottom of the pivoting arm and the spacer may provide some resistance to swinging movement of the gate.

FIG. 10A shows the first face 130 of the gate 48 with the flexible diaphragm 50 having a concave shape relative to the first face 130. The diaphragm 150 is aligned with the larger opening 56 of the gate 48 so that the magnetic assembly 52 is centered within the larger opening 56.

Figure 10B:
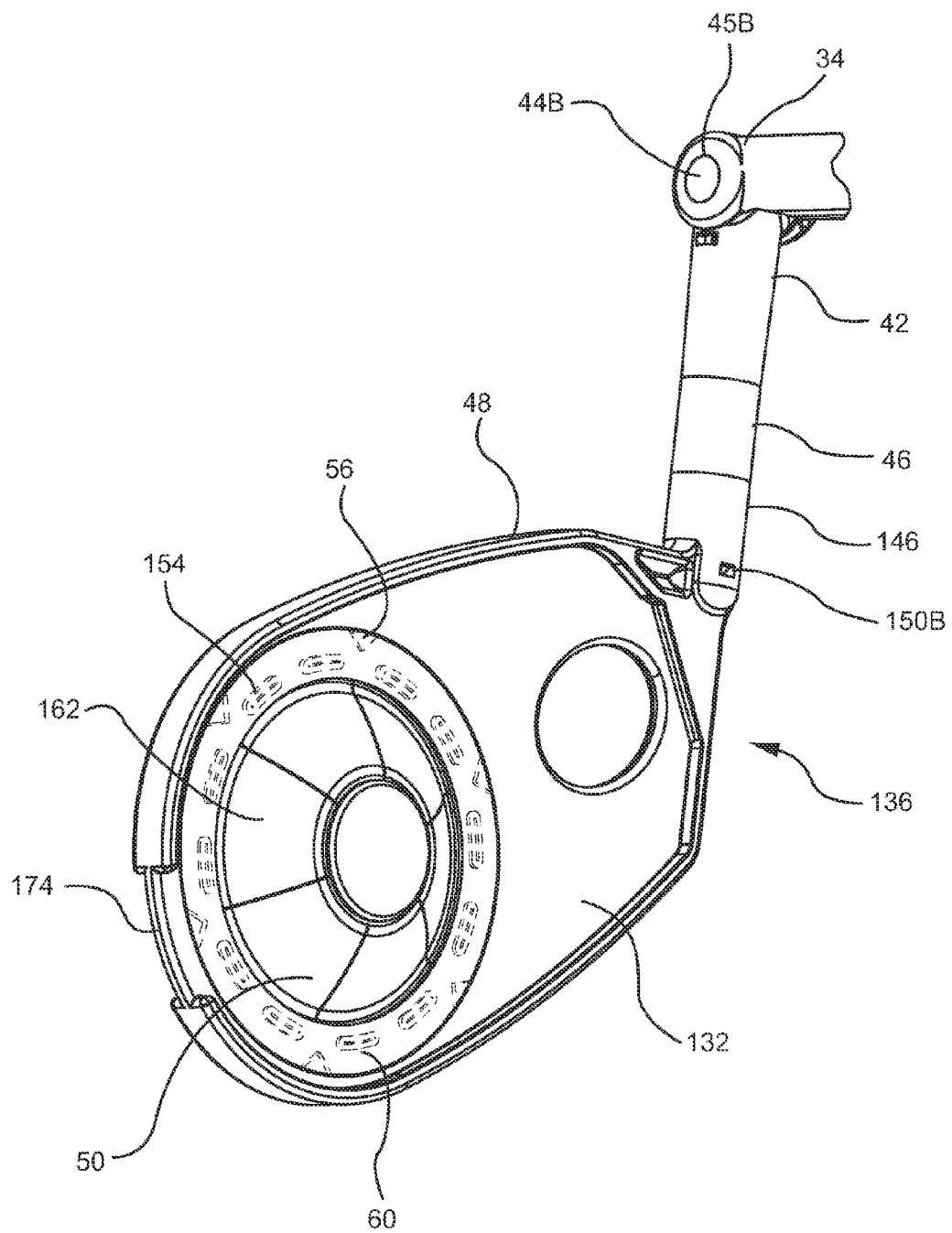
FIG. 10B shows a perspective view of a second face of the swinging gate and the flexible diaphragm shown in FIG. 10A.

FIG. 10B shows the second face 132 of the gate 48 with the flexible diaphragm 50 in the configuration shown in FIG. 10A. The elongated projections 154 extending from the second face of the gate are preferably passed through the elongated openings 174 (FIG. 9A) of the flexible diaphragm 50 for aligning the flexible diaphragm with the larger opening 56. The placement device preferable includes a flexible diaphragm retaining ring 60 that holds the flexible diaphragm within the larger opening 56. When viewing the second face 132 of the swinging gate 48, the dome-shaped portion 162 of the flexible diaphragm 50 has a convex configuration. The magnet assembly 52 is preferably located within the center of the larger opening 56.

Figure 11A:
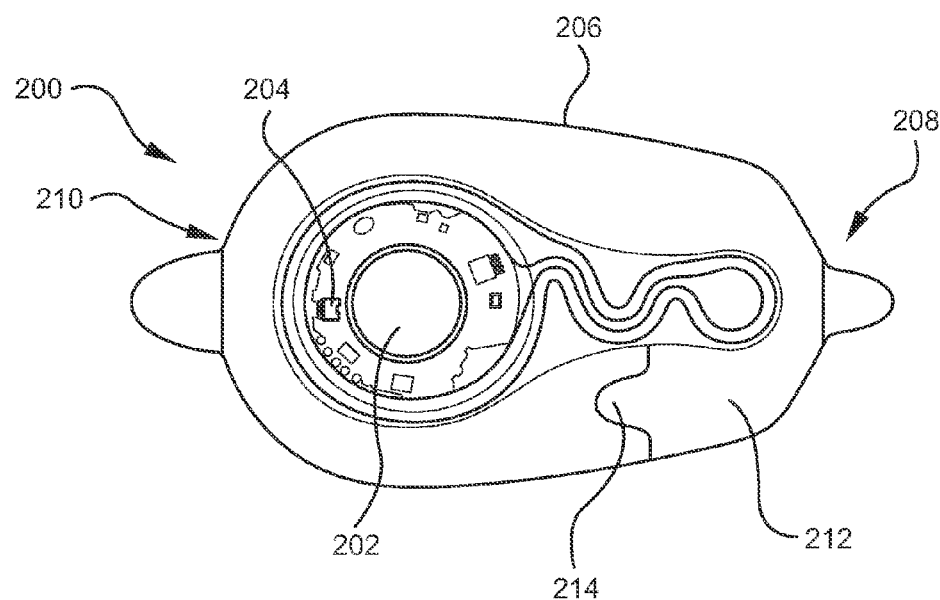
FIG. 11A shows a top plan view of a medical patch, in accordance with one embodiment of the present invention.

Referring to FIG. 11A, in one embodiment, a medical patch 200, such as a selective nerve stimulation (SNS) patch, includes a battery 202 that provides power for the patch and an optical eye 204 that provides a communication interface for controlling the patch. The medical patch 200 preferably has an outer perimeter 206 that extends between a leading end 208 of the medical patch and a trailing end 210 thereof. The medical patch 200 desirably includes a removable top seal 212 that protects the patch during storage and prior to placement on a patient. In one embodiment, the top seal 212 includes a pull tab 214 that may be engaged and pulled for removing the top seal 212.

Figure 11B:
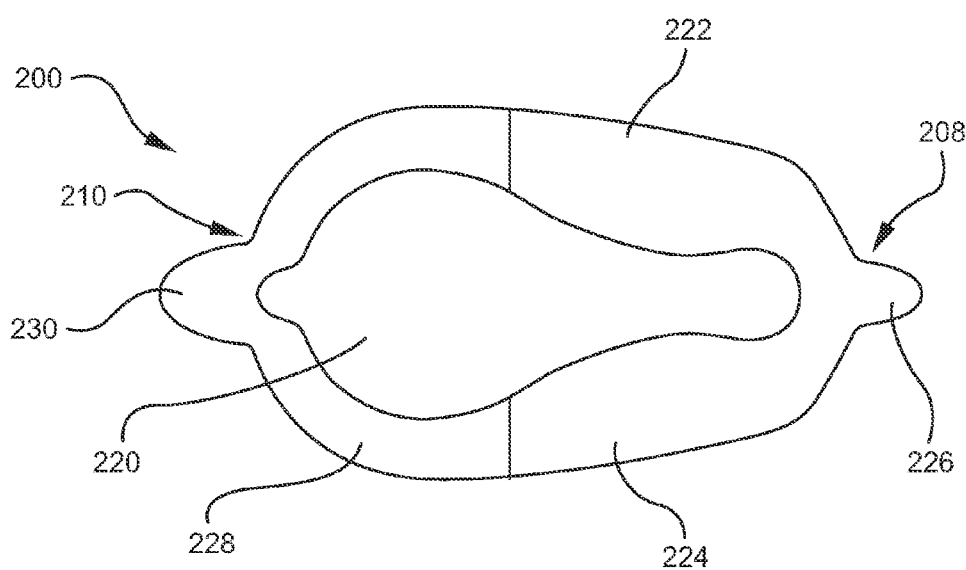
FIG. 11B shows a bottom view of the medical patch shown in FIG. 11A.

FIG. 11B shows a bottom of the medical patch 200 shown in FIG. 11A. In one embodiment, the bottom surface of the medical patch is preferably covered by a central seal 220 that desirably covers one or more electrodes exposed at a bottom surface of the patch, and a bottom seal 222 that covers the bottom surface of the medical patch 200. In one embodiment, the bottom seal 222 includes a first section 224 that covers the leading end 208 of the medical patch and a second section 226 that covers the trailing end 210 of the medical patch 200. The first section 224 of the bottom seal desirably includes a pull tab 226 for removing the first section 224 and exposing the adhesive layer at the bottom of the medical patch 200. The second section 228 of the bottom seal preferably includes a pull tab 230 for removing the second seal section 228. As described herein, the respective pull tabs 226, 230 preferably perform multiple functions including providing alignment of the medical patch 200 with the gate 48 (FIGS. 7A and 7B) and protecting elements provided on the medical patch (e.g. electrodes, adhesive layers) until it is desirable to expose such elements.

In one embodiment, the second pull tab 230 is adapted to be received within the alignment opening 140 formed in the first ridge 138 (FIG. 7A) of the gate. The first pull tab 226 is adapted to be received within one of the rear alignment slots 160A, 160B formed at the trailing end 136 of the gate 48 (FIG. 8B). Thus, the respective first and second pull tabs 226, 230 perform at least two functions. A first function being an alignment function whereby the tabs 226, 230 facilitate alignment of the medical patch 200 on the gate 48. The respective pull tabs 226, 230 also preferably enable the first and second bottom seal sections 224, 228 to be removed after the medical patch has been positioned atop a patient.

Figure 11C:
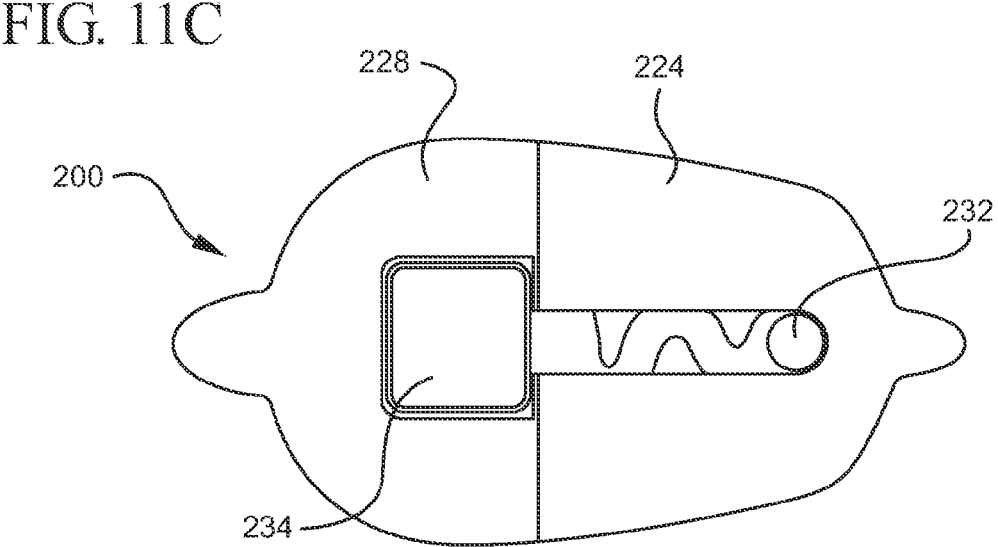
FIG. 11C shows the bottom of the medical patch shown in FIG. 11B after a center seal has been removed for exposing gel pads, in accordance with one embodiment of the present invention.

Referring to FIGS. 11B and 11C, in one embodiment, the central seal 220 may be removed for exposing gel pads 232, 234 accessible at the bottom surface of the medical patch 200. In one embodiment, the gel pads 232, 234 preferably cover electrodes (not shown) so that electrical signals may be transmitted to a patient through the electrodes. In one embodiment, the medical patch generates electrical signals and the gel pads 232, 234 are adapted for helping to pass the electrical signals to one or more nerves of a patient for stimulating one or more nerves In one embodiment, after the central seal 220 has been removed to expose the gel pads 232, 234, the first and second sections 224, 228 of the bottom seal remain in place for protecting the adhesive layer (not shown) provided over the bottom surface of the medical patch 200. In one embodiment, the adhesive layer preferably enables the bottom surface of the medical patch to be adhered to a patient's skin surface.

Figure 12:
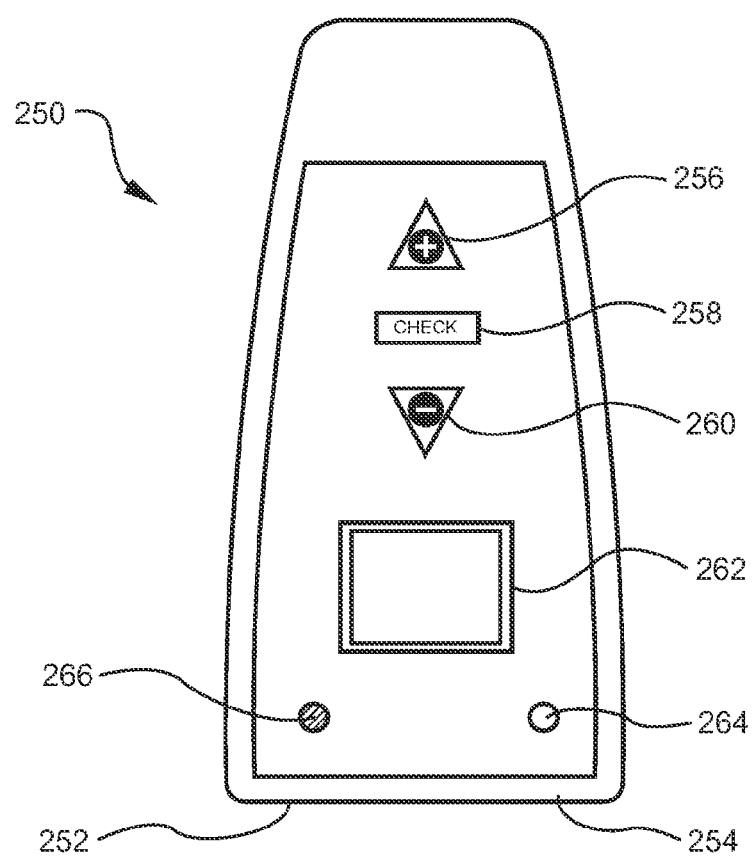
FIG. 12 shows a remote control for communicating with and controlling the medical patch shown in FIGS. 11A-11C, in accordance with one embodiment of the present invention.

Referring to FIG. 12, in one embodiment, a system for placing a medical patch on a patient desirably includes a remote control 250 that is preferably utilized to perform in various functions including to turn a medical patch on and off, to determine the status of the medical patch, and to vary the strength of the signals that the medical patch sends to nerves that control bodily functions, such as bladder function. In one embodiment, the remote control preferably includes an operational end 252 having a communication window 254 that is desirably aimed at the medical patch when a patient desires to activate and/or control the medical patch. In one embodiment, when the remote control is used for communicating with the patch, the communication window 254 must desirably have a clear line of sight to the patch and be within approximately 6-12 inches and more preferably about 8 inches from the medical patch. In one embodiment, the communication window 254 must have a clear line of sight with the medical patch and nothing, such as clothing, may be between the communication window and the medical patch.

In one embodiment, the remote control 250 desirably includes a depressible plus (+) button 256 that may be engaged for increasing the strength of the medical patch's signal. The remote control 250 desirably includes a check button 258 that may be pressed for confirming that the remote control and the patch are working. The check button 258 may also be engaged for confirming that a signal is being sent from the medical patch to the nerves. In one embodiment, the check button 258 may also be used to turn the medical patch ON. The remote control 250 also desirably includes a minus (−) button 260 that may be engaged for decreasing the strength of the medical patch's signal. In one embodiment, the minus (−) button 260 may also engaged for turning the medical patch OFF.

In one embodiment, the remote control 250 preferably includes a visual display 262 that shows the strength of the signal being delivered by the medical patch. In one embodiment, the strength of the medical patch may range from "00" (no signal) to "44" (strongest signal). The visual display 262 may also display error codes if the medical patch is not operating properly. In one embodiment, a user guide and/or troubleshooting guide may be provided that informs a patient about the meaning of the error codes shown in the visual display 262.

In one embodiment, the remote control includes a signal light 264. The signal light 264 preferably blinks yellow to confirm that the medical patch is sending signals to the patient's nerves. In other embodiments, colors other than yellow may be utilized. In addition, in other embodiments, light patterns other than blinking may be utilized to indicate that the patch is functioning properly.

In one embodiment, the remote control 250 includes a status light 266 that lets the patient know that the remote control is successfully "talking" with the medical patch. In one embodiment, the remote control 250 may vibrate or produce a sound to provide an indication that the medical patch and the remote control are in communication (i.e. "talking") to one another. In one embodiment, the status light 266 may show different colors to indicate different operating states of the medical patch. In one embodiment, the status light 266 is green to confirm that the medical patch is ON. In one embodiment, the status light 266 is red to indicate that the medical patch or the remote control has an error. In one embodiment, the status light is yellow to indicate that the remote control is in "sleep mode." In one embodiment, when the remote control is in sleep mode, this status does not affect the settings of the medical patch.

Figure 13A:
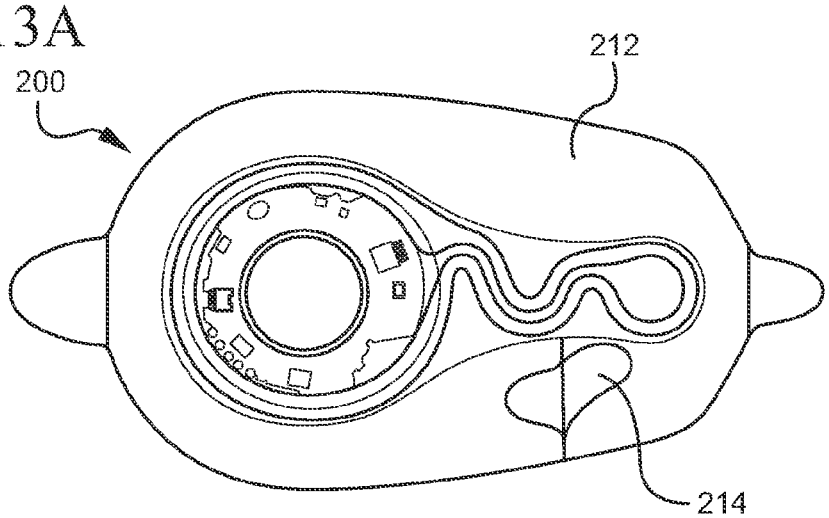
FIGS. 13A-13Q show a method of applying a medical patch on the right side of a patient using the placement tool shown in FIGS. 2A-2D, in accordance with one embodiment of the present invention.
Figure 13B:
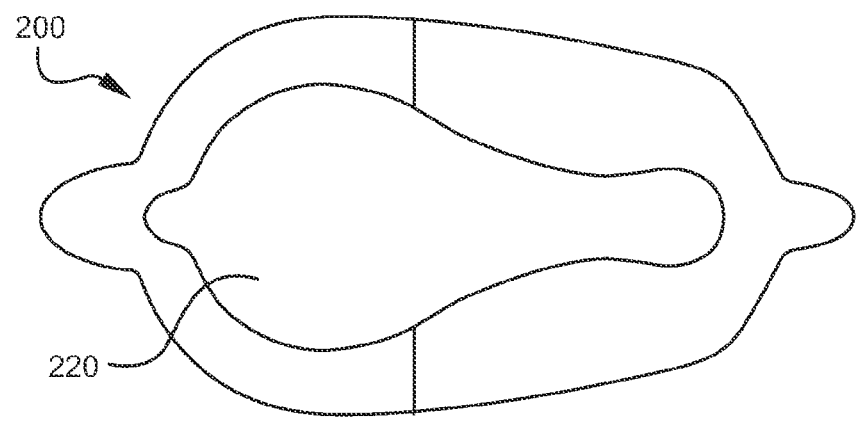
Figure 13C:
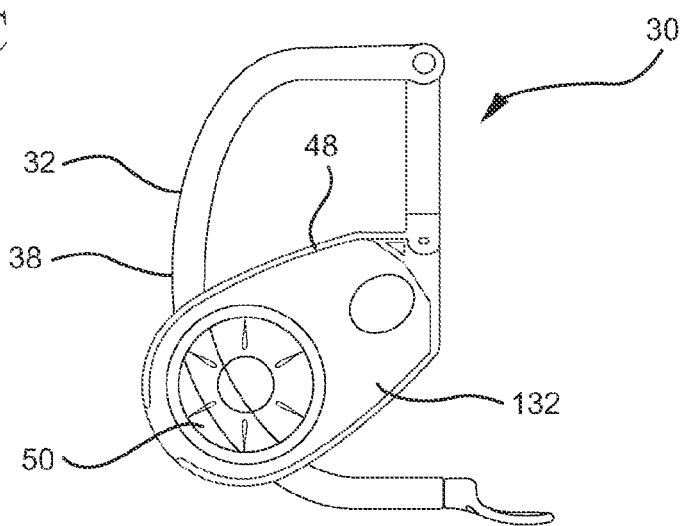
Figure 13D:
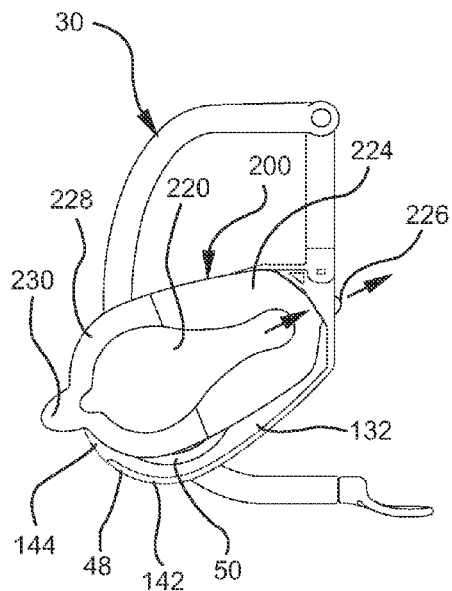
Figure 13E:
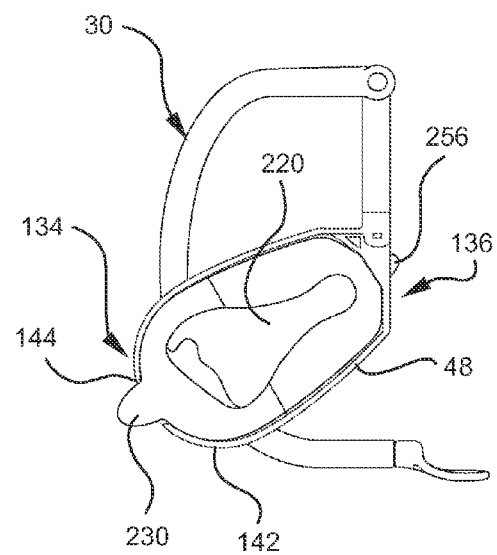
Figure 13F:
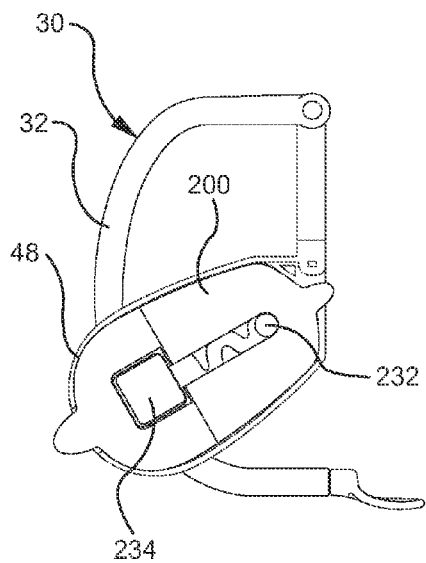
Figure 13G:
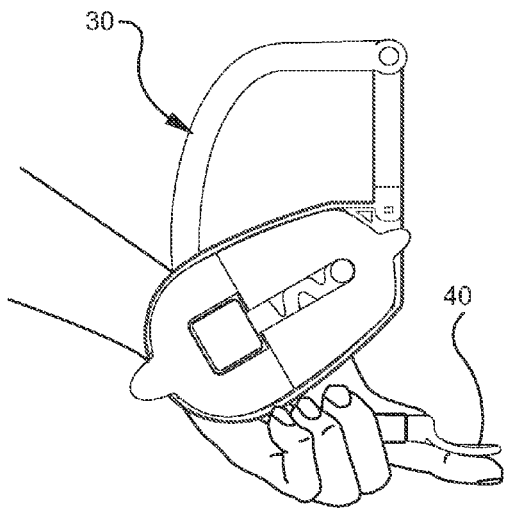
Figure 13H:
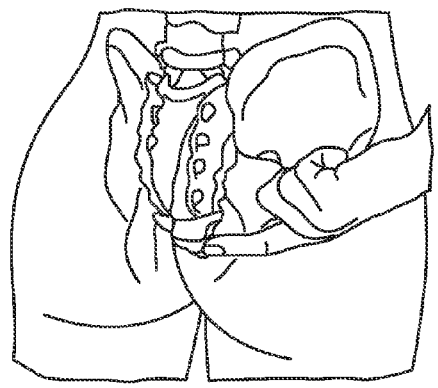
Figure 13I:
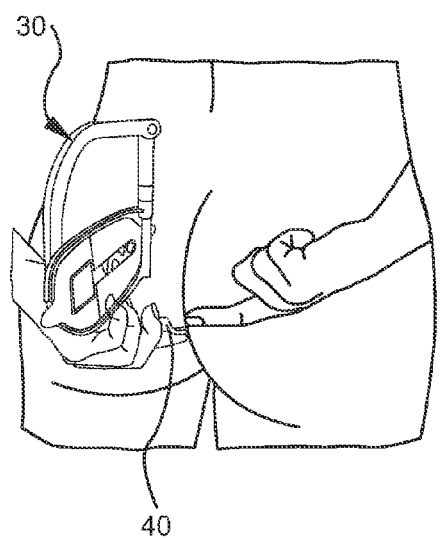
Figure 13J:
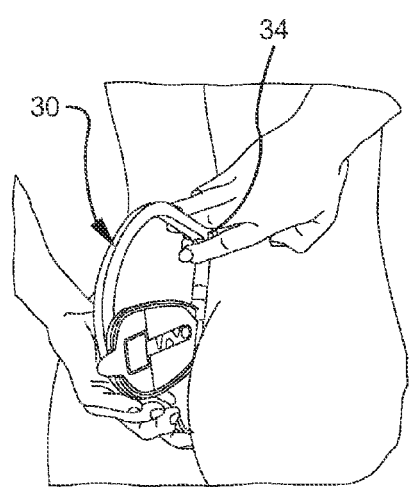
Figure 13K:
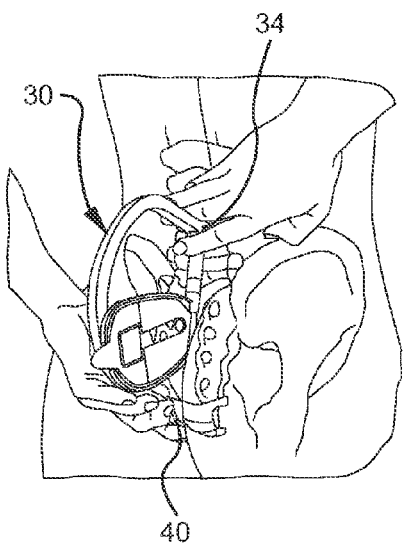
Figure 13L:
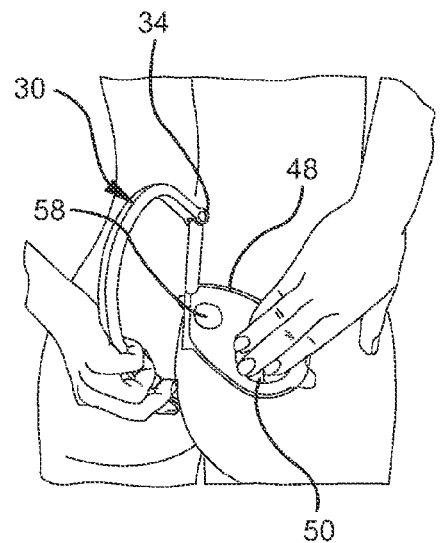
Figure 13M:
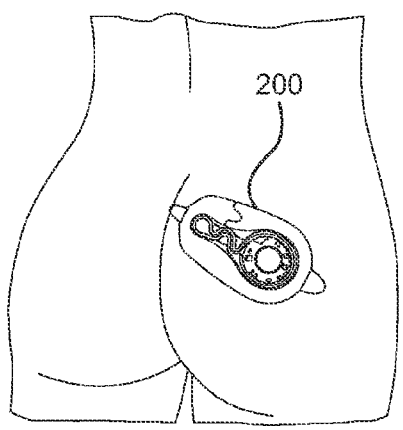
Figure 13N:
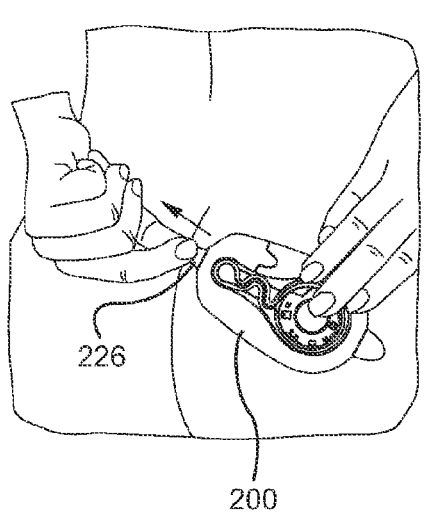
Figure 13O:
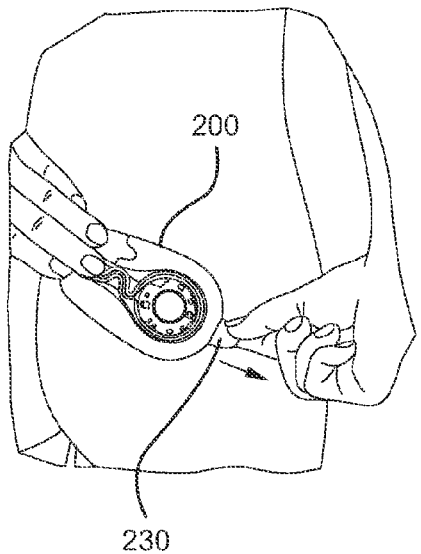
Figure 13P:
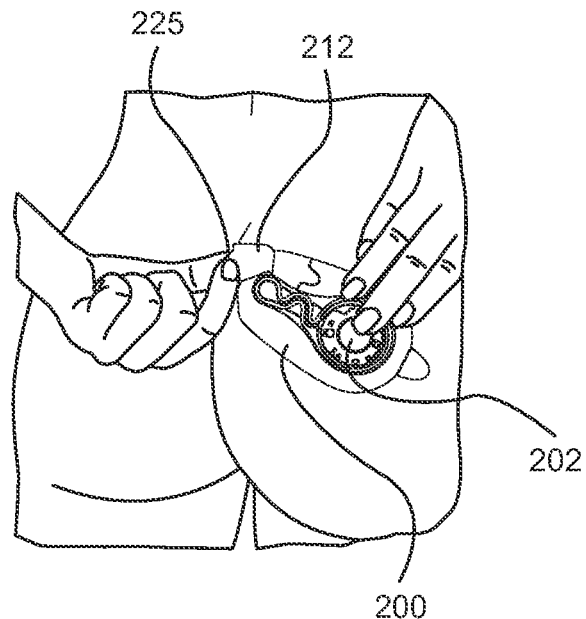
Figure 13Q:
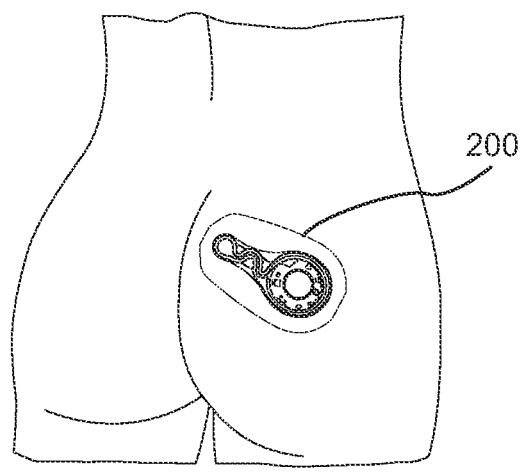

FIGS. 13A-13Q show one method for using a placement device to position a medical patch on a right side of a patient. Referring to FIG. 13A, in one embodiment, the medical patch 200 is preferably removed from a storage pouch, such as a foil pouch. In one embodiment, the patient preferably retains the storage pouch as the pouch will be needed when the medical patch is removed from the patient. In one embodiment, the medical patch 200 is removed from the storage pouch and flexed. As the medical patch 200 is flexed, the patient preferably folds over a pull tab 214 connected with the top seal section 212. After the tab 214 has been folded over as shown in FIG. 13A, the medical patch is placed on a flat surface with the central seal 220 facing up, as shown in FIG. 13B.

In one embodiment, the placement device 30 is readied for receiving a medical patch 200 by swinging the gate 48 into the position shown in FIG. 13C so that it rests against the C-shaped shaft 38 of the handle 32. When the gate 48 is properly swung into place, the placement tool 30 has an appearance that looks like the letter "e." In one embodiment, the placement tool 30 is positioned atop a flat surface with the second face 132 of the gate facing away from the flat surface. The flexible diaphragm 50 is preferably pushed downward so that it assumes the shape of a cup and defines a concave surface that faces up and away from the flat surface. At the same stage, a convex surface of the diaphragm preferably faces down and toward the flat surface.

Referring to FIG. 13D, in one embodiment, the medical patch 200 is loaded on the gate 48 by positioning the top surface of the patch against the second face 132 of the gate 48. In one embodiment, the center seal 220 covering the gel pads at the bottom surface of the medical patch 200 faces up and away from the placement tool 30 and the flat surface supporting the placement tool. In one embodiment, the first pull tab 226 connected with the first bottom seal section 224 is slid into the tab alignment slot 160B (FIG. 8B) at the trailing end of the gate 48. The battery portion of the medical patch (i.e. the raised section of the patch) is placed directly into the concave cup of the flexible diaphragm. The magnetic assembly (not shown) located at the center of the flexible diaphragm 50 preferably holds the battery in the center of the flexible diaphragm. In one embodiment, the trailing pull tab 230 is preferably aligned with the tab alignment slot 144 formed in the second alignment ridge 142. FIG. 13E. shows the medical patch 200 properly loaded onto the gate 48 so that the outer perimeter of the medical patch 200 lies within the alignment ridge 142, with the first pull tab 226 extending through the alignment slot 160B (FIG. 8B) at the trailing end 136 of the gate and the second pull tab 230 sitting within the alignment slot 144 at the leading end 134 of the gate.

Referring to FIGS. 13E and 13F, in one embodiment, the central seal 220 may be removed for exposing the gel pads 232, 234 provided at the bottom surface of the medical patch 200. In one embodiment, a patient applying the patch should take care to not touch the gel pads 232, 234 with unwashed hands or contaminate the gel pads with particles such as lint or dirt. As the patient removes the central seal 220, the patient preferably ensures that the gate 48 remains resting against the handle 32. FIG. 13F shows one embodiment of the present invention whereby the medical patch 200 is properly loaded and positioned within the swinging gate 48 of the placement device 30 and whereby the placement device 30 is properly configured for positioning the medical patch on the right side of the patient.

Referring to FIG. 13G, in one embodiment, a patient holds the placement device 30 with his or her left hand so that the left index finger is underneath the sacral cup 40. Referring to FIG. 13H, in one embodiment, as the patient continues holding the placement tool with the left hand, the patient locates the bottom of the tail bone with his or her right index finger.

Referring to FIG. 13I, in one embodiment, the patient, while maintaining his or her right index finger on the tail bone and left hand on the placement device 30, guides the sacral cup 40 extending from the lower end of the placement device 30 under the patient's right index finger. The spoon shaped top surface of the sacral cup 40 is preferably advanced until it rests under the bottom of the patient's tail bone. At this stage, the patient preferably continues to hold the placement device 30 in place with his or her left hand.

Referring to FIG. 13J, in one embodiment, the patient continues to use his or her left hand to apply upward pressure on the placement device 30 so that the sacral cup 40 rests against the bottom of the tail bone. The patient preferably utilizes his or her right hand and thumb to push the upper end 34 of the placement device against the back until the patient feels the upper end 34 touching the spine.

Referring to FIG. 13K, in one embodiment, after the upper end 34 of the placement device 30 has been pressed against the patient's spine, the patient preferably confirms that the sacral cup 40 remains firmly pressed against the bottom of the tail bone and that the upper end 34 of the placement device 30 is touching the center of the lower spine. If necessary, the patient will preferably adjust the alignment of the placement device 30 so that the upper and lower ends of the placement device are aligned with one another and are substantially aligned with the patient's spine. In one embodiment, the upper and lower ends of the placement device are preferably aligned with a vertical axis that extends along the patient's spine.

Referring to FIG. 13L, in one embodiment, while the patient applies upward pressure with his or her left hand, the patient uses his or her right hand to swing the gate 48 toward the back for abutting the bottom surface of the medical patch against the skin. As the patient swings the gate 48 into the position shown in FIG. 13L, the patient should preferably ensure that the upper end 34 of the placement device does not move relative to the spine. After the gate 48 is swung to the position shown in FIG. 13L, the patient preferably engages the convex surface of the flexible diaphragm 50 located in the larger opening of the gate 48 and presses on the flexible diaphragm to disengage the outer end of the medical patch from the diaphragm. The patient then preferably presses through the smaller opening 58 in the swinging gate to press the inner end of the medical patch away from the smaller opening.

Referring to FIG. 13M, in one embodiment, after the patch has been discharged from the gate, the patient preferably removes the placement device away from the body so that only the medical patch 200 remains in place on the patient. The gel pads (FIG. 13F) provided at the bottom surface of the medical patch 200 preferably adhere the medical patch to the patient's skin. In one embodiment, the patient preferably looks in a mirror to check the position of the medical patch. FIG. 13M shows proper positioning of the patch on the patient, in accordance with one embodiment of the present invention. If the patch is not properly positioned on the patient, the patient may preferably repeat the steps shown in FIGS. 13D-13L for properly positioning the patch on a body.

Referring to FIG. 13N, in one embodiment, the first and second bottom seals covering the adhesive layer on the bottom surface of the medical patch 200 must be removed. In one embodiment, a patient uses his or her right hand to firmly press down on the raised battery portion of the medical patch. While continuing to press down on the raised battery portion of the medical patch, the patient uses his or her left hand to engage the first pull tab 226 and pull the first bottom seal in the direction shown in FIG. 13N so as to remove the first bottom seal and expose a portion of the adhesive layer covered by the seal. As the patient removes the first bottom seal, the patient preferably presses down on the inner portion of the patch from which the first bottom seal was just removed. Moreover, the patient preferably smoothes the patch down to avoid wrinkling.

Referring to FIG. 13O, the patient preferably uses his or her left hand to firmly press down on the left or inner side of the medical patch 200. While continuing to press down on the left side of the patch 200, the patient desirably uses his or her right hand to engage and pull the second tab 230 in the direction shown in FIG. 13O so as to remove the second bottom seal covering the adhesive layer at the bottom surface of the medical patch 200. After the second bottom seal has been removed, the patient desirably presses the right or outer side of the medical patch against the back and desirably smoothes the patch to avoid wrinkling.

Referring to FIG. 13P, in one embodiment, the patient then preferably uses either hand to press down on the raised battery section 202 of the patch. Using the opposite hand, the patient preferably pulls the tab 214 to remove the top seal 212 from the top surface of the patch. The patient may use a circular motion when removing the top seal 212 for exposing the top surface of the medical patch 200. Referring to 13Q, in one embodiment, after the top seal has been removed, the patient preferably presses the patch down on the skin so that it adequately adheres to the skin. The patient may use either hand to smooth the patch. In one embodiment, the patient may use a circular motion to smooth the patch and ensure that it adheres to the skin.

Although FIGS. 13A-13Q show the placement device being used to place medical patches over a lower region of the back or spine, it is contemplated that the placement device disclosed herein may be used to place medical patches anywhere on the patient's spine. It is also contemplated that the placement device may be modified to place medical patches on a patient's anterior region including the chest and abdominal regions. It is also contemplated that the present invention may be used anywhere on the body where it is desirable to place medical patches on opposite sides of the patient's body at approximately the same vertical location on the patient.

In one embodiment, after the patch has been applied as shown in FIG. 13Q, the patient may use the remote control shown and described herein to control and operate the medical patch 200. In one embodiment, the patient is required to alternate the patch placement on opposite sides of the back. In one embodiment, the alternate patch placement occurs every week. For example, in one embodiment, a new patch may be applied and worn on the right side of the back for seven days. At the end of seven days, the patient may use the remote control to turn the patch off and use his or her fingernails to peel up a peripheral edge of the medical patch. The patch may then be peeled away from the skin and any adhesive remaining on the skin may be cleaned away. After the medical patch has been removed, the patch is preferably put back into the original storage pouch and returned to a health care provider for further handling.

Figure 14D:
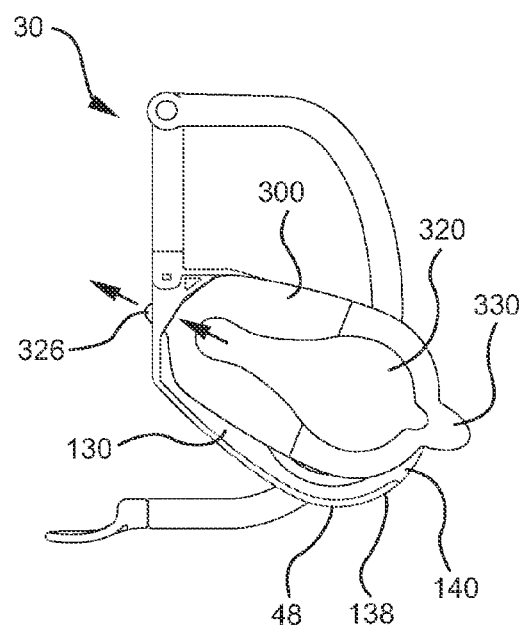
FIGS. 14A-14Q show a method of applying a medical patch on the left side of a patient using the placement device shown in FIGS. 2A-2D, in accordance with one embodiment of the present invention.
Figure 14E:
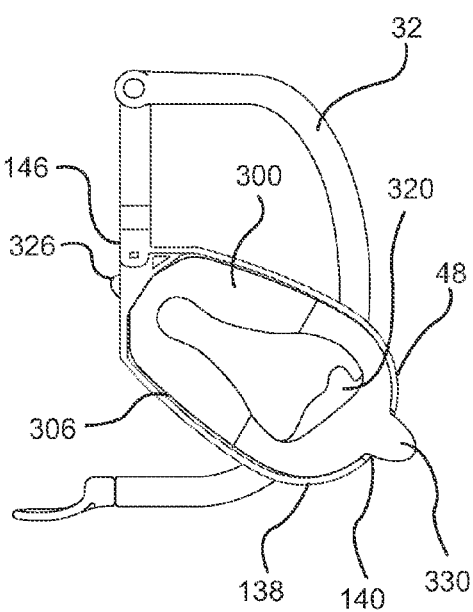
Figure 14F:
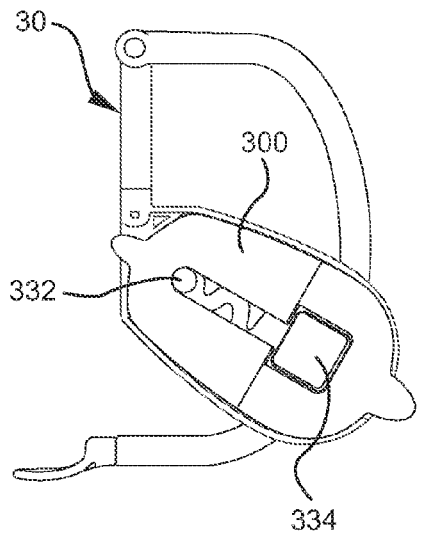
Figure 14G:
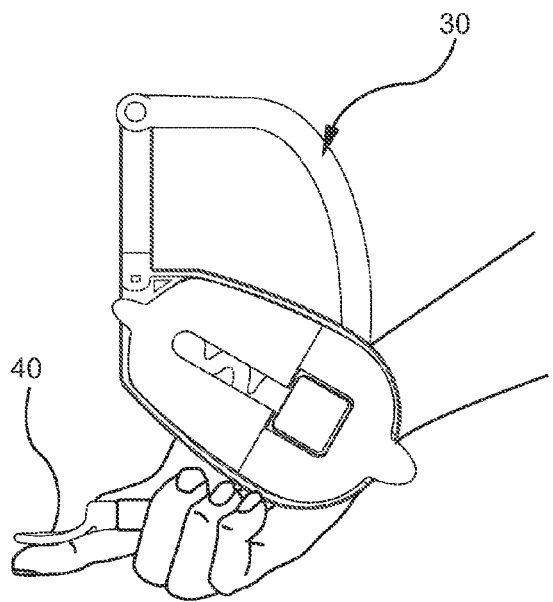
Figure 14H:
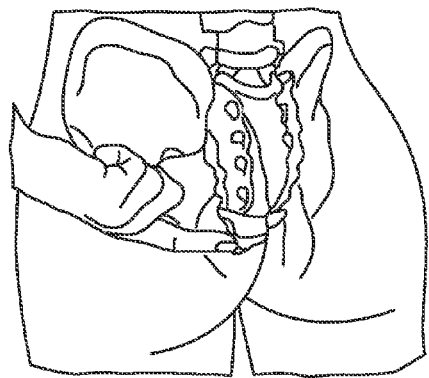
Figure 14I:
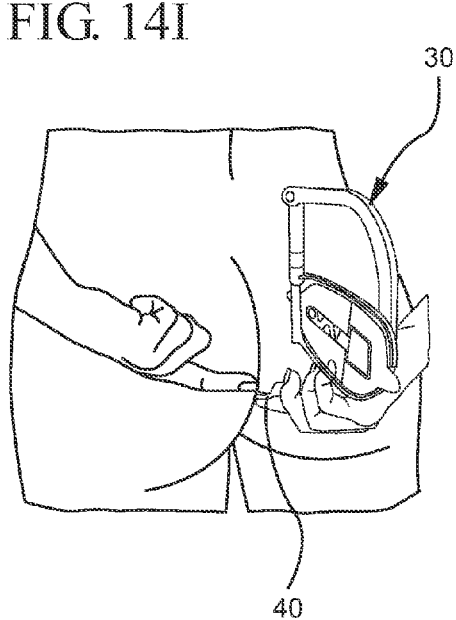
Figure 14J:
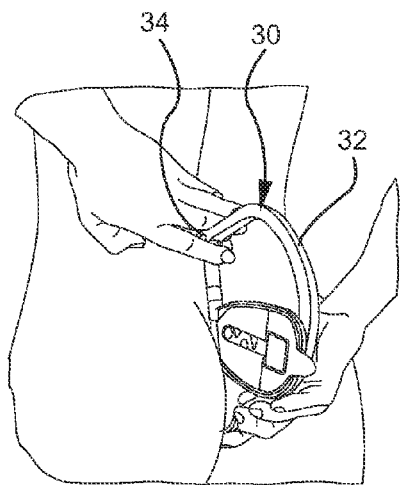
Figure 14K:
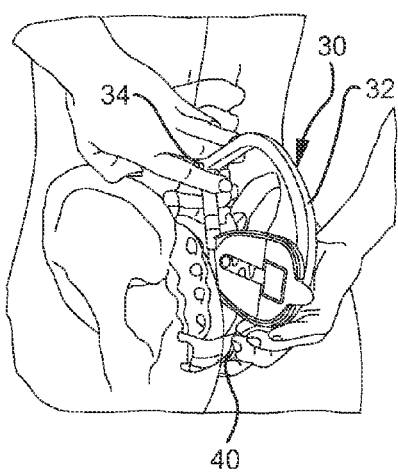
Figure 14L:
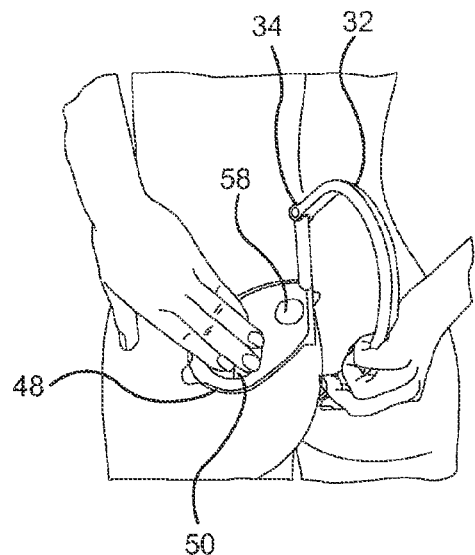
Figure 14M:
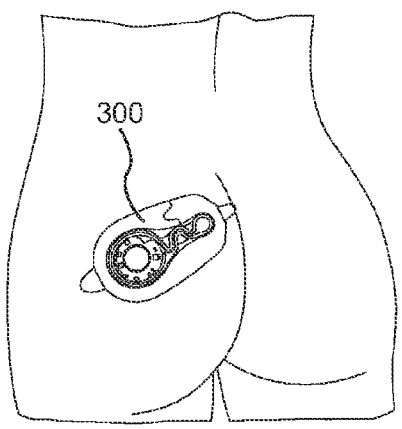
Figure 14N:
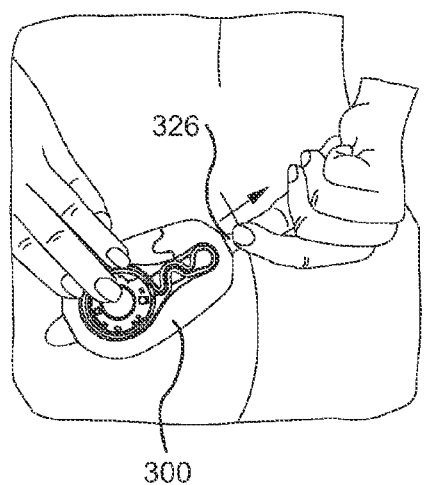
Figure 14O:
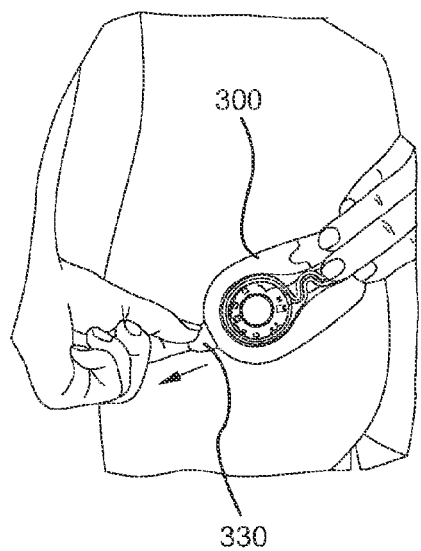
Figure 14P:
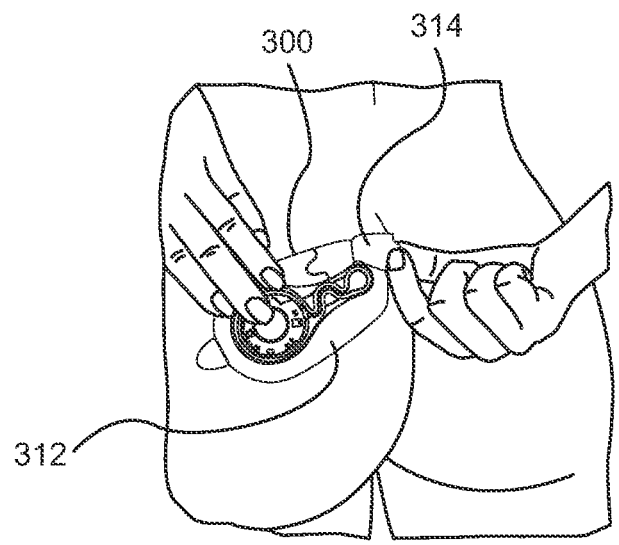
Figure 14Q:
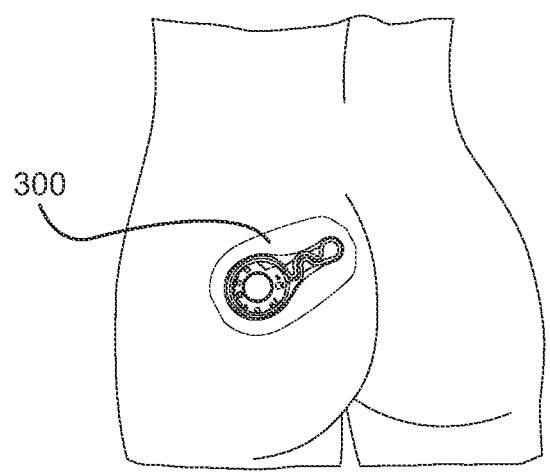

FIGS. 14A-14Q show a method for placing a replacement medical patch on a left side of a patient's back. Referring to FIG. 14A, in one embodiment, a second replacement medical patch 300 includes a battery 302 for providing power to the medical patch and an optical eye 304 for communicating with the remote control. The medical patch has an outer periphery 306 that extends between a leading end 308 and a trailing end 310 thereof. The medical patch 300 preferably includes a top surface that is covered by a top seal 312. The top seal preferably includes a pull tab 314 that may be pulled for removing the top seal 312 from the top surface of the medical patch 300.

In one embodiment, the replacement patch 300 is prepared for application by removing the patch from a storage pouch. The medical patch 300 is preferably flexed and the pull tab 314 is desirably folded over on top of the patch. The replacement medical patch 300 is desirably placed atop a flat surface so that the central seal 320 covering the bottom of the patch is exposed and facing away from the flat surface. The adhesive layer (not shown) on the bottom surface of the patch 300 is preferably covered by a first bottom seal 324 that covers the leading edge 308 of the medical patch. The first bottom seal 324 desirably includes a pull tab 326 for removing the first bottom seal and exposing the adhesive layer under the first bottom seal. The bottom surface of the medical patch 300 is also preferably covered by a second bottom seal 328 that may be removed using a second pull tab 330 located adjacent the trailing end 310 of the medical patch 300. When desired, the second pull tab 320 may be pulled to remove the second bottom seal 328 and expose the adhesive layer under the second bottom seal.

Referring to FIG. 14C, in one embodiment, the handle 32 of the placement device 30 is positioned atop a flat surface and the gate 40 is swung so that it rests against the C-shaped shaft 38 of the handle 32. When the gate 48 is swung into the proper position for applying a medical patch on the left side of a patient, the placement device 30 preferably looks like a backward letter "e." With the placement device positioned atop the flat surface in the position shown in FIG. 14C, the flexible diaphragm 50 is preferably pushed so that is assumes a cup shape. In other words, the flexible diaphragm 50 defines a concave surface that faces away from the flat surface supporting the placement device 30.

Referring to FIG. 14D, in one embodiment, with the central seal 320 facing up, the medical patch 300 is loaded into the swinging gate 48 of the placement device 30. In one embodiment, the first pull tab 326 connected with the first bottom seal is placed in the slot 160A (FIG. 8A) formed at the trailing end of the first face 130 of the gate. The second pull tab 330 connected with the second bottom seal is aligned with the alignment gap 140 formed in the alignment ridge 138 that projects above the first face 130.

Referring to FIG. 14E, in one embodiment, after the replacement patch 300 has been properly loaded into the gate 48, the outer periphery 306 of the medical patch 300 preferably lies within the alignment ridge 138 projecting from the first face of the gate. The first pull tab 326 preferably extends through one of the alignment slots formed adjacent the shaft 146 of the gate, and the trailing pull tab 330 is preferably aligned with the gap 140 extending between the alignment ridge 138.

In one embodiment, the central bottom seal 320 is preferably pulled from the bottom surface of the patch to expose one or more gel pads accessible at the bottom surface of the medical patch. As noted above, patients should not touch the gel pads with unwashed hands and should avoid getting any contaminants such as lint or dirt on the gel pads. In one embodiment, as the patient pulls away the central seal 320, the gate 48 preferably rests against the handle 32.

FIG. 14F shows the placement device 30 in the proper configuration for applying the replacement medical patch 300 to the left side of a patient's back. The gel pads 332, 334 accessible at the bottom surface of the replacement medical patch 300 are exposed for providing electrical signals for stimulating one or more of the patient's nerves.

Referring to FIG. 14G, in one embodiment, a patient holds the placement tool 30 with his or her right hand with the right index finger underneath the sacral cup 40. Referring to FIG. 14H, in one embodiment, the patient preferably uses his or her left index finger to locate the bottom of the tail bone. Referring to FIG. 14I, while maintaining the left index on the tail bone, and the right hand on the placement tool 30, the patient preferably advances the sacral cup 40 to a position whereby it is under the patient's left index finger. The patient then preferably removes the left index finger so that the concave top surface of the sacral cup 40 preferably rests comfortably under the patient's tail bone.

Referring to FIG. 14J, in one embodiment, while continuing to hold the placement device 30 in place with his or her right hand, the patient uses his or her left hand and thumb to push the upper end 34 of the handle 32 against his or her back until the upper end 34 touches the patient's spine. Referring to FIG. 14K, in one embodiment, the patient preferably undertakes an alignment check whereby the patient ensures that the sacral cup 40 remains firmly under the tail bone and that the upper end 34 of the handle 32 is touching the center of the lower spine. If necessary, the patient may adjust the position of the placement device 30 so that it is substantially vertically aligned with the spine.

Referring to FIG. 14L, in one embodiment, while the patient applies upward pressure with his or her right hand, the patient uses his or her left hand to swing the gate 48 toward the back until the bottom surface of the medical patch is against the skin. As the patient swings the gate 48 toward the skin, the patient will desirably ensure that the upper end 34 of the handle 32 does not move away from the spine. In one embodiment, the patient preferably uses his or her left hand to firmly press on the flexible diaphragm 50 so as to detach the outer end of the medical patch from the gate 48. The patient then preferably utilizes his or her fingers on the left hand to pass through the smaller opening 58 to detach the inner end of the medical patch from the gate 48.

Referring to FIG. 14M, in one embodiment, after the patient pushes through the larger and smaller openings in the gate to detach the medical patch 300 from the gate, the patient may move the placement device away from the bottom so that only the medical patch 300 remains in contact with the back. The patient preferably inspects the position of the replacement medical patch 300 to confirm that the patch is in the correct position. In one embodiment, if the patch is not in the position shown in FIG. 14M, the patient may repeat the steps described above in FIGS. 14A-14L for properly positioning the replacement medical patch.

At the stage shown in FIG. 14M, the one or more gel pads (not shown) accessible at the bottom surface of the medical patch adhere the patch to the patient's skin. In order to more firmly and reliably adhere the replacement medical patch to the patient's skin, the first and second bottom seals must be removed so as to expose the adhesive layer covering at least a portion of the bottom surface of the patch.

Referring to FIG. 14N, in one embodiment, the patient uses his or her left hand to firmly press down on the raised battery portion of the medical patch 300. While continuing to press down with the left hand, the patient uses his or her right hand to engage and pull the first pull tab 326 in the direction shown in FIG. 14N. As the patient removes the first pull tab 326, the first bottom seal is removed to expose at least a portion of the adhesive layer covering the bottom surface of the medical patch. After the first bottom seal is removed, the patient should preferably press the patch down on the back so that the adhesive layer adheres the patch to the patient's skin. In one embodiment, the patient also preferably gently smoothes the medical patch to avoid wrinkling.

Referring to FIG. 14O, in one embodiment, the patient preferably utilizes his or her right hand to firmly press down the right or inner side of the medical patch 300. While pressing down with the right hand, the patient desirably uses his or her left hand to pull the second tab 330 connected with the second bottom seal. Removing the second bottom seal preferably exposes the adhesive layer covering at least a portion of the bottom surface of the medical patch. As the second bottom seal is removed, the patient desirably utilizes his or her right hand to press the patch down on the back and may gently smooth the patch to avoid wrinkling. In one embodiment, the patient should preferably wait approximately 3-5 minutes before proceeding to the nest stage of the application process.

Referring to FIG. 14P, in one embodiment, a patient use either hand to press down upon the raised battery part of the medical patch 300. The patient may use his or her other hand to grasp the tab 314 connected with the top seal 312 that covers the top surface of the patch. The patient may pull the tab 314 to remove the top seal from the top surface of the patch. In one embodiment, the patient may use a circular motion for removing the top seal 312.

Referring to FIG. 14Q, in one embodiment, a patient desirably presses the patch down on the skin to form a good attachment with the skin. In one embodiment, a patient might use either hand and may use a circular motion to smooth the patch.

Figure 15A:
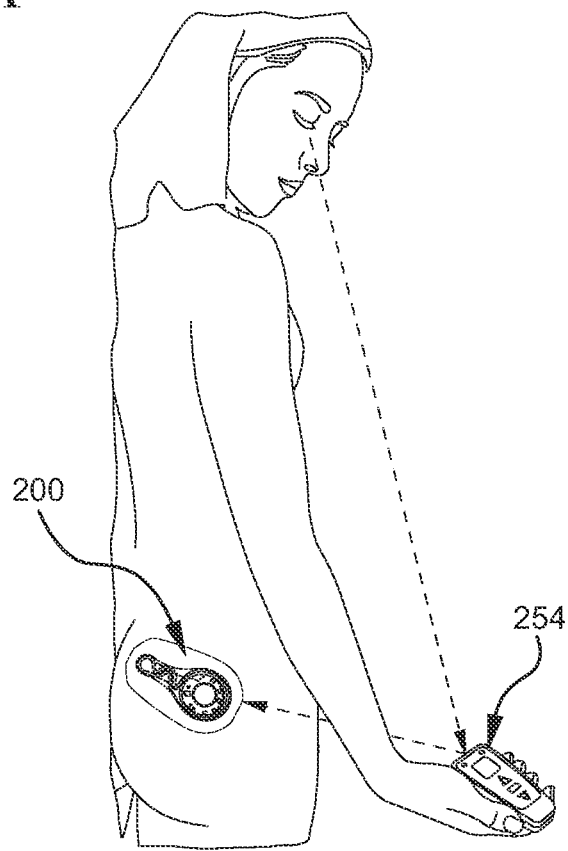
FIGS. 15A and 15B show a method of using a remote control for operating a medical patch, in accordance with one embodiment of the present invention.
Figure 15B:
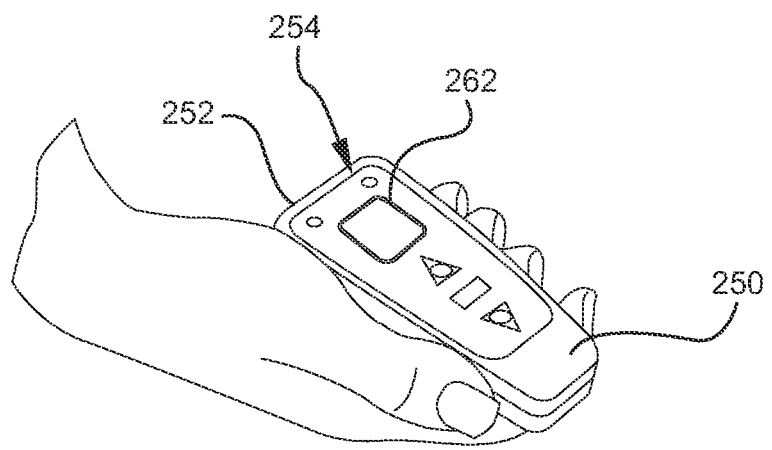

Referring to FIGS. 15A and 15B, in one embodiment, a patient may use a remote control 250 for activating a medical patch. As shown in FIG. 15A, the patient desirably picks up the remote control 250 with her hand. In one embodiment, the signals from the remote control 250 may not penetrate through clothing. As such, the patient may be required to expose the area of the back where the patch is attached when attempting to activate the patch. The optical window 254 at the signaling end 252 of the remote control 250 is desirably aimed toward the patch 200. In one embodiment, the remote control is desirably held on the same side of the body as the patch and is preferably held within 6-12 inches and more preferably within 8 inches from the patch. As shown in FIG. 15B, the patient preferably holds the remote control 250 so that the patient may observe the visual display 262 provided on the remote control. The patient may desirably activate and control the medical patch while holding the remote control 250 in the position shown in FIGS. 15A and 15B.

Figure 16A:
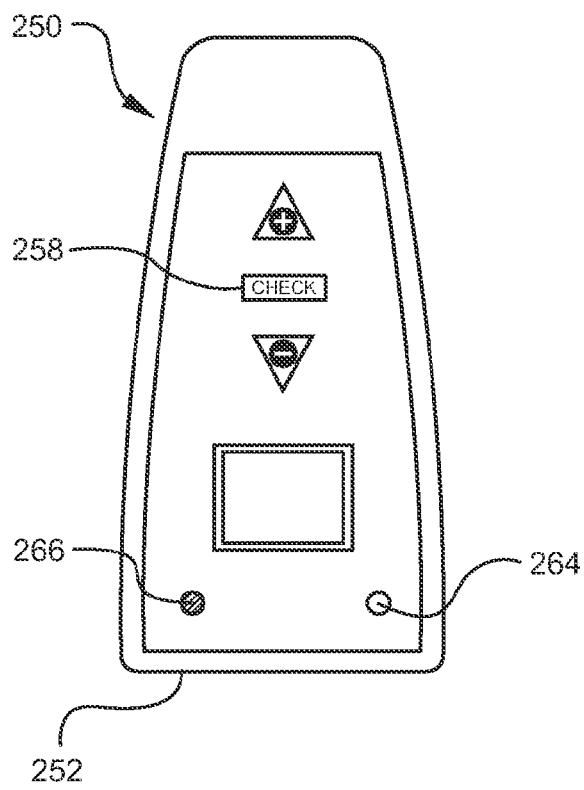
FIGS. 16A-16C show a method of using a remote control to activate a medical patch, in accordance with one embodiment of the present invention.

Referring to FIG. 16A, in on embodiment, the patient may turn the patch ON by pressing and hold down the check button 258 on the remote control 250. In one embodiment, the patient holds down the check button 258 for approximately two seconds. In one embodiment, as the patient holds down the check button 258, the patient will feel the remote control 250 vibrate, which signals that the remote control 250 is talking with the medical patch.

In one embodiment, if the remote control 250 does not vibrate and the signal light 264 does not illuminate, a patient may try aiming the working end 252 of the remote control at the medical patch from a different angle. When the different angle is attained, the patient may then press and hold down on the check button 258 once again. If the signal light 264 remains OFF or if the status light 266 is red, the patient may refer to a troubleshooting guide to determine any problems that may be occurring.

Figure 16B:
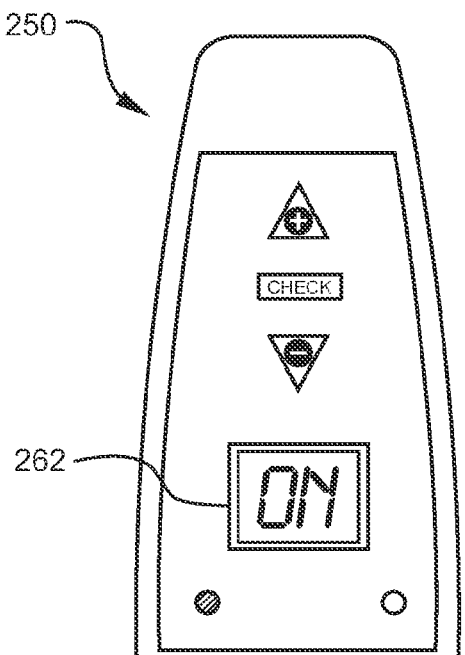

Referring to FIG. 16B, in one embodiment, the patient maintains the working end 252 of the remote control aimed the medical patch. In one embodiment, within a period of time such as three additional seconds, the patient will feel the remote control 250 vibrate once again, which indicates that the medical patch is ON. The patient may also observe the visual display 262, which preferably provides an additional indicator that the medical patch is ON.

Figure 16C:
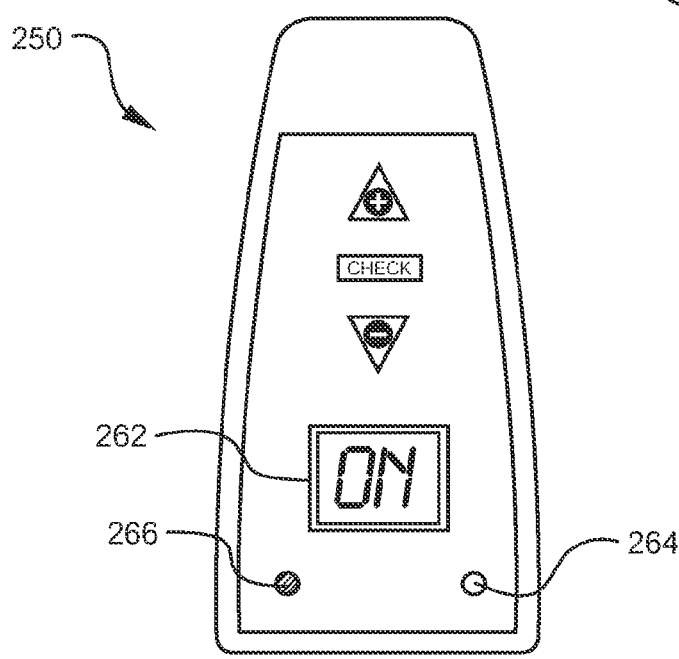

Referring to FIG. 16C, in one embodiment, a patient may look at the front face of the remote control 250 to confirm that the medical patch has been turned ON. In one embodiment, the signal light 264 on the front face of the remote control is preferably blinking yellow and the status light 266 is desirably green. In addition, the visual display 262 preferably reads "ON."

Figure 17A:
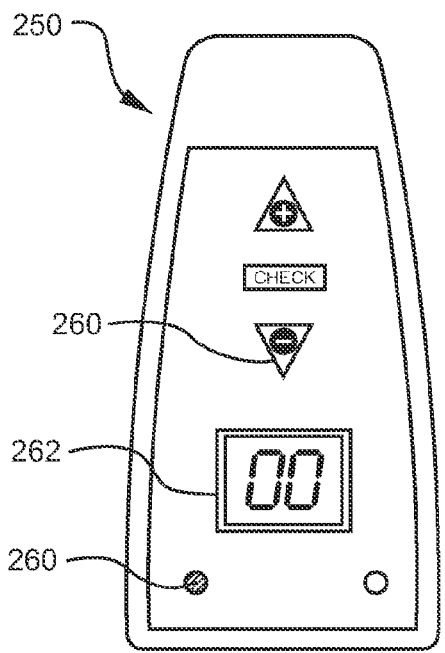
FIGS. 17A-17C show a method using a remote control to de-activate a medical patch, in accordance with one embodiment of the present invention.
Figure 17B:
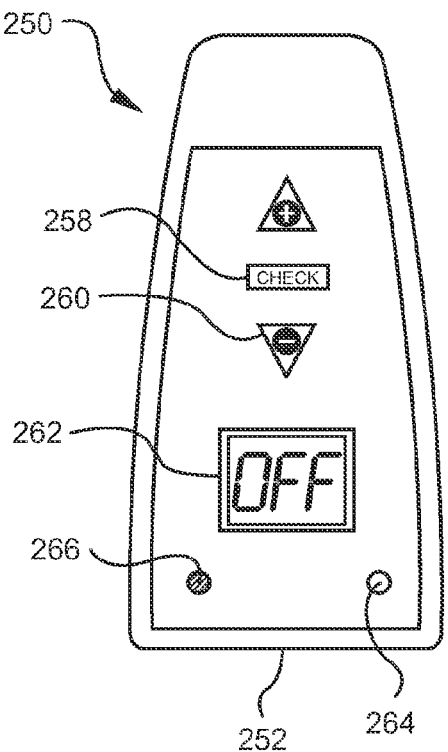
Figure 17C:
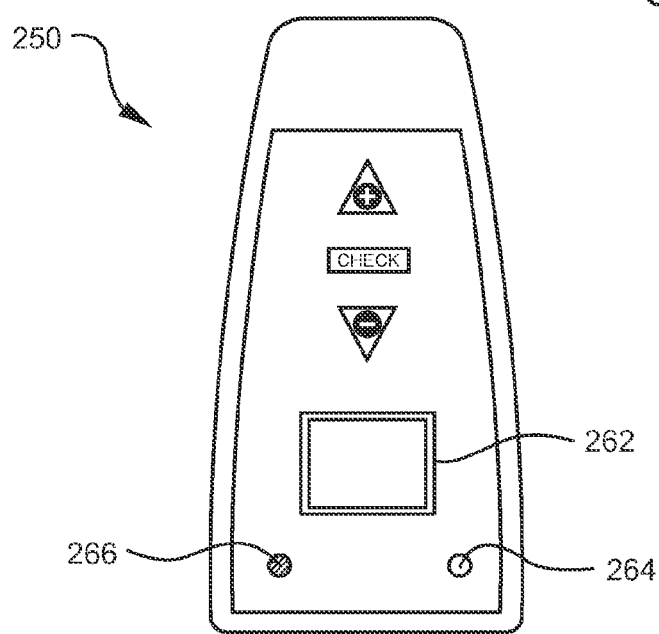

Referring to FIGS. 17A-17C, in one embodiment, the remote control 250 may also be used to turn the medical patch OFF. Referring to FIG. 17A, in one embodiment, the patient may press and hold down the minus (−) button 260 until the visual display 262 reads "00." At this stage, the medical patch is preferably ON, however, it is not sending any electrical signals to the nerves of the body. At this stage of deactivating the medical patch, the status light 266 is desirably blinking green. Referring to FIG. 17B, in one embodiment, the patient may hold the minus (−) button 260 down for a period of time such as at least two seconds. At that stage, the remote control 250 will desirably vibrate as the patch is turned OFF. In one embodiment, if the remote control 250 does not vibrate after the minus (−) button 260 has been held down for a period of time, the patient should preferably look at the signal light 264. If the signal light 264 is OFF, the patient should preferably try to aim the working end 252 of the remote control 250 at the medical patch from a different angle. At that point, the patient should preferably press and hold down the check button 258 again. If the signal light 264 remains off, or if the status slight 266 is red, the patient should preferably refer to a troubleshooting guide.

Referring to FIG. 17C, in one embodiment, the patient should preferably look at the front face of the remote control 250 to confirm that the medical patch is OFF. In one embodiment, the signal light 264 is preferably deactivated, and the status light 266 is preferably illuminated, such as being illuminated the color green. The visual display 262 is desirably inactive and does not display any information.

Figure 18A:
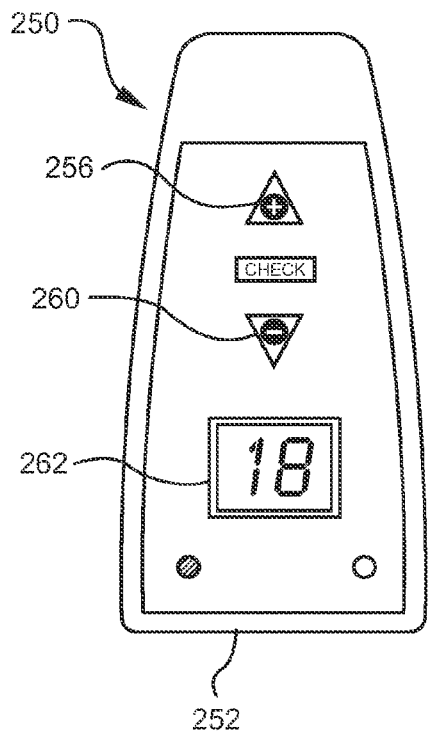
FIGS. 18A and 18B show a method of using a remote control for increasing and decreasing the signal strength of a medical patch, in accordance with one embodiment of the present invention.
Figure 18B:
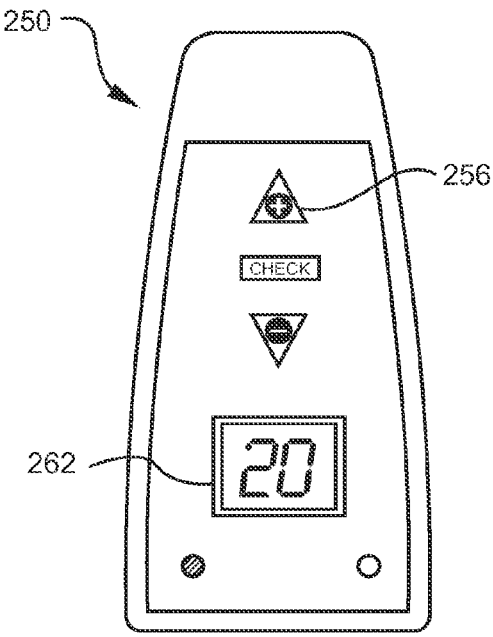

Referring to FIGS. 18A and 18B, in one embodiment, the remote control 250 may be used to increase and decrease the signal strength generated by the medical patch. In one embodiment, the patient may pick up the remote control and aim the working end 252 toward the medical patch.

Referring to FIG. 18A, in one embodiment, in order to increase the signal strength generated by the medical patch, the patient presses and holds down the plus (+) button 256. In order to decrease the signal strength generated by the medical patch, the patient should press and hold down the minus (−) button 260. In one embodiment, a quick press of either the plus (+) button 256 or the minus (−) button 260 will either increase or decrease the signal strength by one number on the visual display 262. In one embodiment, for every additional second that the patient holds down either button, the signal strength will desirably change by two numbers.

Referring to FIG. 18C, in one embodiment, the patient has pressed down the plus button 256 two times to increase the signal strength from 18 (FIG. 18A) to 20 (FIG. 18B). In one embodiment, the signal strength shown in the visual display 262 may range from "00" at the lower end to "44" at the upper end.

Figure 19:
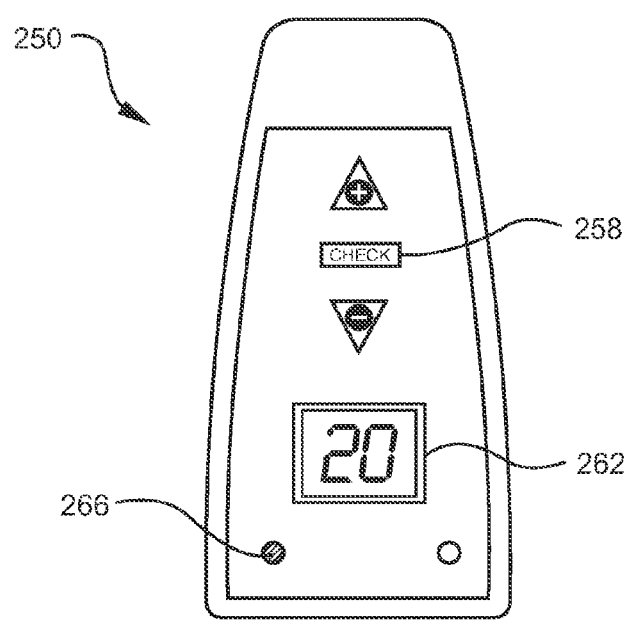
FIG. 19 shows a method of using a remote control to check the status of a medical patch, in accordance with one embodiment of the present invention.

Referring to FIG. 19, in one embodiment, a patient may utilize the remote control 250 to determine whether the remote control is communicating with the medical patch and/or whether the medical patch is sending an electrical signal to the patient's nerves. In one embodiment, a patient may check the status of the medical patch by pressing the check button 258, which will show the signal strength in the visual display 262. The status light 266 will preferably provide a determination of whether the remote control 250 is communicating with the medical patch. If the status light 266 is illuminated green, the remote control and the medical patch are communicating. If the status light 266 is illuminated red, this is an indication that the remote control and the medical patch are not communicating and the patient should refer to the troubleshooting manual.

In one embodiment, a trouble shooting guide may be provided to a patient for operating a medical patch using a remote control. One preferred trouble shooting guide provides:

| Status Light | Signal Light | Signal Display | What to do |
| --- | --- | --- | --- |
| No light * ○ | No light * ○ | Any | Check that:<br>☒ The remote control is not in sleep mode. If you press any button, the signal display should show a number or ".." to say that the remote control is on. If nothing happens, replace the batteries |
| Red ● | No light * ○ | | ☒ Be sure nothing (like clothing) is getting in the way and keeping the remote control from talking to the patch<br>☒ Confirm that the pointer window of the remote control is directed toward the patch.<br>☒ Confirm that the remote control is within 12 inches of the patch |
| Red ● | Yellow ◉ | 51-53 | Replace the patch. Go to pages 14-20 to see steps for placing the patch on the right side of your body Go to pages 21-27 to see steps for placing the patch on the left side of your body |
| Red ● | Yellow ◉ | 70-71, 73-77 | Replace the remote control. Call your healthcare provider to get a new one. Do not try to fix it. |
| Red ● | Yellow ◉ | "LO" or 72 | Call your healthcare provider to replace the remote control. |

* No light means no light when any button is pressed while the remote control is aimed at the patch.

The invention disclosed herein is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although one embodiment of the present invention is described in relation to nerve stimulation in females, it is to be understood that it can be readily adapted for use in males, and children. The inventive principles, apparatus and methods disclosed herein may also have application for stimulating various other nerves, either independently or simultaneously, such as stimulation of nerves during labor and delivery, or selectively stimulating branches of a given nerve bundle to selectively address different patient conditions. Thus, the present invention can, for example, be used to selectively treat or affect one or more of the following conditions simultaneously: stress urinary incontinence, anal and fecal incontinence, pain, sexual dysfunction, interstitial cystitis, chronic pain such as but not limited to pelvic pain, nocturia, and gastrointestinal disorders such as but not limited to gastric pacing. Finally, the present invention as described herein can also be used to stimulate body parts other than nerves, such as glands that secrete hormones, and large muscle groups, such as biceps muscle stimulation associated with physical therapy.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

The selective nerve stimulation patch of the present invention is designed to be stored for prolonged periods before use. Thus, it is essential that the patch is constructed so that there is no premature contact between the battery and the circuitry until the patch is intentionally activated. Therefore, the patch desirably has a one-time activated sealed switch mechanism. The switch mechanism may have several designs, including a reed switch that is normally "off" in the presence of a magnet (contained in the package), an over-center switch mechanism that could be mechanically toggled from a normally-off to a normally-on state, a switch like that described above where initial contact is maintained by a conductive adhesive, or a battery contact arrangement that prevents normal circuit completion until intentionally pressed by the end user.

In one or more embodiments of the present invention, a selective nerve stimulation patch is adapted to generate a modulated waveform for stimulating a target nerve using the devices and techniques described in commonly assigned United States Patent Application Publication Nos. US 2005/0277998 (U.S. application Ser. No. 11/146,522, filed Jun. 7, 2005), and US 2006/0195153 (U.S. application Ser. No. 11/343,627, filed Jan. 31, 2006), the disclosures of which are hereby incorporated by reference herein. The waveform is desirably generated by modulating a carrier waveform with a pulse envelope. Properties of the carrier waveform such as amplitude, frequency, and the like, are chosen so as to overcome the tissue impedance and the stimulation threshold of the target nerve. The pulse envelope is a waveform having a specific pulse width, amplitude and shape designed to selectively stimulate the target nerve. This waveform is able to penetrate efficiently through the tissue to reach the target nerve with minimal loss in the strength of the electrical signal, thereby saving battery power that would otherwise have been used in several attempts to stimulate the target nerve with low frequency signals. Moreover, only the target nerve is stimulated, and non-target nerves are not stimulated.

In one embodiment of the present invention, an underlying principal of operation is that nerves within the body can be selectively targeted for stimulation without affecting adjacent neurons. As is well known to those skilled in the art, bioelectric potentials are produced as a result of electrochemical activity of excitable cells found within nervous system tissue. These excitable cells exist in two electrical states, resting potential or action potential. Cells remain in the resting potential state until adequate stimulus is provided to cause the cells to reach the action or threshold potential, at which time the nerve "fires," and the action potential travels at a constant conduction velocity unattenuated along the cell membranes. This all-or-nothing response of the action potential causes the cell's membrane potential to go through a characteristic repeatable cycle, where the potential first goes from the negative resting potential, to a positive action potential, and then back down to the negative resting potential again all within approximately 1 ms. The response remains the same regardless of the magnitude of the stimulus, so long as the stimulus exceeds the threshold potential.

Since neurons in the human body do vary greatly in diameter, length and myelination, the capacitance and conduction velocity (operating frequency) for these neurons vary as well. Using the differences in physical characteristics of adjacent neurons, selected nerves can be targeted for stimulation without affecting adjacent neurons. That is, selective neural stimulation can be achieved by characterizing the frequency response (capacitance) of adjacent neurons, and tuning the stimulation frequency to an area of no-overlap. For example, for two adjacent neurons, where neuron A has a frequency band of operation from 0-20 Hz and neuron B has a frequency band of operation from 20-30 Hz, neuron B can be selectively stimulated with no effect on neuron A. Further, neuron A can be selectively stimulated even in an overlapping frequency range if stimulation is applied during neuron B's absolute refractory period, during which no amount of stimulation will cause neuron B to fire as discussed above, or if the stimulation is less than the magnitude required to cause stimulation during the relative refractory period. As described further herein, these principles can be applied to achieve selective stimulation of two or more nerves within the body.

By the system and method described above, individual components of the modulated signal package can be used to selectively target different nerves, different nerve branches, different muscles, or selected other body parts. That is, a single nerve stimulation patch could provide stimulation signals designed to relieve multiple different symptoms such as those associated with pain management, overactive bladder, fecal incontinence, interstitial cystitis and any other pelvic floor disorder.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A placement device that enables a patient to self-locate and position a medical patch on the patient's body comprising:
    an alignment guide including a C-shaped shaft having a first end with a first anatomical alignment marker and a second end with a second anatomical alignment marker;
    a swinging gate both pivotally and rotationally coupled with the first end of said shaft for selectively pivoting said swinging gate within a plane toward and away from said shaft and selectively rotating said swinging gate between opposite sides of said shaft, wherein said gate comprises a first major face, a second major face, and a first opening extending through said gate between said first and second major faces;
    an adjustable spacer coupling said gate with the first end of said shaft for selectively adjusting spacing between said gate and the first end of said shaft;
    a flexible diaphragm disposed within said first gate opening, wherein said flexible diaphragm includes a flexible dome that is adapted to be selectively pressed through said first gate opening for transforming the shape of said flexible diaphragm between a concave cup facing said first face of said gate and a convex dome facing said first face of said gate; and at least one magnet located in a center of said flexible dome for holding a medical patch within said flexible diaphragm.

2. The placement device as claimed in claim 1, wherein said swinging gate is rotatable to the left of said shaft for placing a medical patch on a left side of a patient and to the right of said shaft for placing a medical patch on a right side of a patient.

3. The placement device as claimed in claim 1, further comprising a medical patch having an active region that is adapted to deliver neurostimulation, pain-management agents, hormones, or pharmacological agents to a target location on a patient.

* * * * *